US012485210B2

(12) United States Patent
Poppe et al.

(10) Patent No.: US 12,485,210 B2
(45) Date of Patent: Dec. 2, 2025

(54) HEMODIALYSIS SYSTEM INCORPORATING DIALYSATE GENERATOR

(71) Applicant: DIALITY INC., Irvine, CA (US)

(72) Inventors: Clayton Poppe, Irvine, CA (US); Osman Khawar, Irvine, CA (US)

(73) Assignee: DIALITY INC., Irvine, CA (US)

( * ) Notice: Subject to any disclaimer, the term of this patent is extended or adjusted under 35 U.S.C. 154(b) by 465 days.

(21) Appl. No.: 17/087,383

(22) Filed: Nov. 2, 2020

(65) Prior Publication Data

US 2021/0128807 A1 May 6, 2021

Related U.S. Application Data

(60) Provisional application No. 62/930,858, filed on Nov. 5, 2019.

(51) Int. Cl.
*A61M 1/16* (2006.01)
*A61M 60/50* (2021.01)

(52) U.S. Cl.
CPC ........ *A61M 1/1656* (2013.01); *A61M 1/1696* (2013.01); *A61M 60/50* (2021.01); *A61M 1/1647* (2014.02); *A61M 2205/502* (2013.01)

(58) Field of Classification Search
CPC .............. A61M 1/1647; A61M 1/1656; A61M 1/1696; A61M 2205/502; A61M 60/50
See application file for complete search history.

(56) References Cited

U.S. PATENT DOCUMENTS 5,643,205 A 7/1997 Utterberg
8,459,292 B2 6/2013 Wilt et al.
8,499,780 B2 8/2013 Wilt et al.
8,580,112 B2 11/2013 Updyke et al.
(Continued)

FOREIGN PATENT DOCUMENTS

WO WO 2015/183981 A2 12/2015
WO 2016006274 1/2016
(Continued)

OTHER PUBLICATIONS

WO, PCT/US20/58342 ISR and Written Opinion, Feb. 1, 2021.
EP, EP 20885866.2 Extended European Search Report, Nov. 9, 2023.

*Primary Examiner* — Dirk R Bass
(74) *Attorney, Agent, or Firm* — ONE LLP

(57) ABSTRACT

A portable hemodialysis system is provided including a dialyzer, a closed loop blood flow path which transports blood from a patient, to the dialyzer, and back to the patient, and a closed loop dialysate flow path which transports dialysate through the dialyzer. The hemodialysis system includes a hemodialysis machine and dialysate generator which are physically connectable to, and disconnectable from, one another. To connect the hemodialysis machine and dialysate generator together, both the hemodialysis machine and dialysate generator possess connectable and disconnectable electrical connectors and fluid connectors which are positioned and constructed to allow both a fluid and electrical connection between the two machines. The hemodialysis machine includes a processor and a user interface, preferably in the form of a touchscreen, that is capable of controlling both the functions of the hemodialysis machine and the dialysate generator.

3 Claims, 19 Drawing Sheets

(56) References Cited

U.S. PATENT DOCUMENTS

| | | | | |
|---|---|---|---|---|
| 8,985,133 | B2 | 3/2015 | Grant et al. | |
| 8,992,189 | B2 | 3/2015 | Wilt et al. | |
| 9,649,419 | B2 | 5/2017 | Giordano | |
| 9,677,554 | B2 | 6/2017 | Wilt et al. | |
| 9,951,768 | B2 | 4/2018 | Grant et al. | |
| 2009/0127193 | A1* | 5/2009 | Updyke | A61M 1/3472 210/636 |
| 2010/0192686 | A1* | 8/2010 | Kamen | A61M 1/15 715/764 |
| 2010/0326916 | A1* | 12/2010 | Wrazel | A61M 1/16 210/205 |
| 2011/0105983 | A1 | 5/2011 | Kelly et al. | |
| 2011/0189048 | A1* | 8/2011 | Curtis | G16H 20/40 210/85 |
| 2015/0196699 | A9 | 7/2015 | Wilt et al. | |
| 2017/0143868 | A1 | 5/2017 | Huang et al. | |
| 2018/0207345 | A1 | 7/2018 | Peters | |
| 2018/0250462 | A1* | 9/2018 | Groder | A61M 1/1664 |
| 2019/0167885 | A1 | 6/2019 | Kelly et al. | |

FOREIGN PATENT DOCUMENTS

| | | |
|---|---|---|
| WO | 2017140431 | 8/2017 |
| WO | 2018234198 | 12/2018 |

* cited by examiner

HEMODIALYSIS SYSTEM INCORPORATING DIALYSATE GENERATOR

RELATED APPLICATIONS

The present application claims priority to U.S. Provisional Patent Application Ser. No. 62/930,858 filed on Nov. 5, 2019.

BACKGROUND OF THE INVENTION

The present invention relates to an artificial kidney system for use in providing dialysis. More particularly, the present invention is directed to a hemodialysis system which incorporates a machine for generating dialysate.

Applicant hereby incorporates herein by reference any and all patents and published patent applications cited or referred to in this application.

Hemodialysis is a medical procedure that is used to achieve the extracorporeal removal of waste products including creatine, urea, and free water from a patient's blood involving the diffusion of solutes across a semipermeable membrane. Failure to properly remove these waste products can result in renal failure.

During hemodialysis, the patient's blood is removed by an arterial line, treated by a dialysis machine, and returned to the body by a venous line. The dialysis machine includes a dialyzer containing a large number of hollow fibers forming a semipermeable membrane through which the blood is transported. In addition, the dialysis machine utilizes a dialysate liquid, containing the proper amounts of electrolytes and other essential constituents (such as glucose), that is also pumped through the dialyzer.

Dialysate solution, also commonly referred to as dialyzing fluid, is an aqueous electrolyte solution that is similar to the found in extracellular fluid with the exception of the buffer bicarbonate and potassium. Dialysate solution is almost an isotonic solution having an osmolality of approximately 300±20 milliosmoles per liter (mOsm/L). To ensure patient safety and prevent red blood cell destruction by hemolysis or crenation, the osmolality of dialysate must be close to the osmolality of plasma which is 280±20 mOsm/L. Dialysate solution commonly contains six (6) electrolytes: sodium (Na+), potassium (K+), calcium (Ca2+), magnesium (Mg2+), chloride (Cl—), and bicarbonate. Dialysate also contains a seventh component, the nonelectrolyte glucose or dextrose. The dialysate concentration of glucose is commonly between 100 and 200 mg/dL.

Typically, dialysate is prepared by mixing clean water with appropriate proportions of an acid concentrate and a bicarbonate concentrate. Preferably, the acid and the bicarbonate concentrate are separated until the final mixing right before use in the dialyzer as the calcium and magnesium in the acid concentrate will precipitate out when in contact with the high bicarbonate level in the bicarbonate concentrate. The clean water for using in making the dialysate must be relatively pure such as by processing municipal drinking water through a water purification system to acceptable purification levels.

Water purification is the process of removing undesirable chemicals, biological contaminants, suspended solids, and gases from water in order to reduce the concentration of particulate matter including suspended particles, parasites, bacteria, algae, viruses, and fungi as well as reduce the concentration of a range of dissolved and particulate matter. The water purification methods used include physical processes such as filtration, sedimentation, and distillation; biological processes such as slow sand filters or biologically active carbon; chemical processes such as flocculation and chlorination; and the use of electromagnetic radiation such as ultraviolet light.

The dialysis process across the membrane is achieved by a combination of diffusion and convection. The diffusion entails the migration of molecules by random motion from regions of high concentration to regions of low concentration. Meanwhile, convection entails the movement of solute typically in response to a difference in hydrostatic pressure. The fibers forming the semipermeable membrane separate the blood plasma from the dialysate and provide a large surface area for diffusion to take place which allows waste, including urea, potassium and phosphate, to permeate into the dialysate while preventing the transfer of larger molecules such as blood cells, polypeptides, and certain proteins into the dialysate.

Typically, the dialysate flows in the opposite direction to blood flow in the extracorporeal circuit. The countercurrent flow maintains the concentration gradient across the semipermeable membrane so as to increase the efficiency of the dialysis. In some instances, hemodialysis may provide for fluid removal, also referred to as ultrafiltration. Ultrafiltration is commonly accomplished by lowering the hydrostatic pressure of the dialysate compartment of a dialyzer, thus allowing water containing dissolved solutes, including electrolytes and other permeable substances, to move across the membrane from the blood plasma to the dialysate. In rarer circumstances, fluid in the dialysate flow path portion of the dialyzer is higher than the blood flow portion, causing fluid to move from the dialysis flow path to the blood flow path. This is commonly referred to as reverse ultrafiltration. Since ultrafiltration and reverse ultrafiltration can increase the risks to a patient, ultrafiltration and reverse ultrafiltration are typically conducted while supervised by highly trained medical personnel.

Unfortunately, hemodialysis suffers from numerous drawbacks. Among the drawbacks is that large quantities clean dialysate must be available. Typically, this is done by preparing dialysate onsite at a hospital or dialysis center which treats a large population of patients. Unfortunately, hospital and in-center dialysis treatments require that a patient travel from their home for three treatments a week with each treatment typically takes about 3 to 4 hours. Further, a patient must make appointments for these treatments requiring that their schedules be set long in advance, which effects their standard of living. Furthermore, hemodialysis treatments will often leave a patient suffering from nausea, cramping, dizziness, and headaches, and yet, they must coordinate and endure traveling home to recover.

To a lesser extent, patients conduct hemodialysis at home. This reduces scheduling concerns, and the burden of traveling to and from a clinic. However, home hemodialysis requires more frequent treatments which are typically done for two hours, six days a week. These treatments require that large quantities of heave dialysate be shipped to the patient. Alternatively, a patient's home must be equipped with a water purification system and the patient must prepare the dialysate themselves. Unfortunately, current water purification systems suitable for preparing dialysate are expensive, often loud, and take up a good deal of living space.

Home hemodialysis suffers from still additional disadvantages. Current home dialysis systems are big, complicated, intimidating and difficult to operate. The equipment requires significant training. Home hemodialysis systems are currently too large to be portable, thereby preventing hemodialysis patients from traveling. Home hemodialysis systems are expensive and require a high initial monetary investment, particularly compared to in-center hemodialysis where patients are not required to pay for the machinery. Present home hemodialysis systems do not adequately provide for the reuse of supplies, making home hemodialysis economically less feasible to medical suppliers. As a result of the above-mentioned disadvantages, very few motivated patients undertake the drudgery of home hemodialysis.

Accordingly, there is a significant need for a hemodialysis system that is transportable, lightweight, easy to use, patient-friendly and thus capable of in-clinic or in-home use.

Moreover, it would be desirable to provide a hemodialysis system that incorporates a water purification system.

In addition, it would be desirable to provide a hemodialysis system that generated dialysate.

Aspects of the present invention fulfill these needs and provide further related advantages as described in the following summary.

SUMMARY OF THE INVENTION

According to a first aspect of the invention, a hemodialysis system which includes a hemodialysis machine and a dialysate generator. The hemodialysis machine and a dialysate generator each include their own housing and are connectable and disconnectable to one another by electrical connectors and fluid connectors. Moreover, it is preferred that the hemodialysis machine and dialysate generator may be operated together, and the hemodialysis machine and dialysate generator may operate and function independent of the other.

The hemodialysis machine includes an arterial blood line for connecting to a patient's artery for collecting blood from a patient, a venous blood line for connecting to a patient's vein for returning blood to a patient, and a disposable dialyzer. The arterial blood line and venous blood line may be typical constructions known to those skilled in the art. For example, the arterial blood line may be traditional flexible hollow tubing connected to a needle for collecting blood from a patient's artery. Similarly, the venous blood line may be a traditional flexible tube and needle for returning blood to a patient's vein. Various constructions and surgical procedures may be employed to gain access to a patient's blood including an intravenous catheter, an arteriovenous fistula, or a synthetic graft.

Preferably, the disposable dialyzer has a construction and design known to those skilled in the art including a blood flow path and a dialysate flow path. The term "flow path" is intended to refer to one or more fluid conduits, also referred to as passageways, for transporting fluids. The conduits may be constructing in any manner as can be determined by those skilled in the art, such as including flexible medical tubing or non-flexible hollow metal or plastic housings. The blood flow path transports blood in a closed loop system by connecting to the arterial blood line and venous blood line for transporting blood from a patient to the dialyzer and back to the patient. Meanwhile, the dialysate flow path transports dialysate in a closed loop system from a supply of dialysate to the dialyzer and back to the dialysate supply.

Preferably, the hemodialysis system contains one or more reservoirs for storing a dialysate solution. In one embodiment of the hemodialysis system, the one or more reservoirs are located in the hemodialysis machine. For this embodiment, the reservoir connects to the hemodialysis machine's dialysate flow path to form a closed loop system for transporting dialysate from the reservoir to the hemodialysis machine's dialyzer and back to the reservoir. More preferably, the hemodialysis machine possesses two (or more) dialysate reservoirs which can be alternatively placed within the dialysate flow path. When one reservoir possesses contaminated dialysate, dialysis treatment can continue using the other reservoir while the reservoir with contaminated dialysate is emptied and refilled. The reservoirs may be of any size as required by clinicians to perform an appropriate hemodialysis treatment. However, it is preferred that the two reservoirs be the same size and sufficiently small so as to enable the dialysis machine to be easily portable. Acceptable reservoirs are 0.5 liters to 5.0 liters in size. The preferred reservoir stores approximately 2.0 liters of dialysate.

The hemodialysis machine preferably possesses one or more heaters thermally coupled to the reservoirs for heating dialysate stored within the reservoir. In addition, the hemodialysis machine includes temperature sensors for measuring the temperature of the dialysate within the reservoirs. The hemodialysis machine preferably possesses a fluid level sensor for detecting the level of fluid in the reservoir. The fluid level sensor may be any type of sensor for determining the amount of fluid within the reservoir. Acceptable level sensors include magnetic or mechanical float type sensors, conductive sensors, ultrasonic sensors, optical interfaces, and weight measuring sensors such as a scale or load cell for measuring the weight of the dialysate in the reservoir.

Preferably, the hemodialysis machine includes three primary pumps. Two of the pumps are first and second "dialysate" pumps which are connected to the dialysate flow path for pumping dialysate through the dialysate flow path from a reservoir to the dialyzer and back to the reservoir. Preferably, a first pump is positioned in the dialysate flow path "upflow", (meaning prior in the flow path) from the dialyzer while the second pump is positioned in dialysate flow path "downflow" (meaning subsequent in the flow path) from the dialyzer. Meanwhile, the hemodialysis machine's third primary pump is connected to the blood flow path. This "blood" pump pumps blood from a patient through the arterial blood line, through the dialyzer, and through the venous blood line for return to a patient. It is preferred that the third pump be positioned in the blood flow path, upflow from the dialyzer.

The hemodialysis machine may also contain one or more sorbent filters for removing toxins which have permeated from the blood plasma through the semipermeable membrane into the dialysate. Filter materials for use within the filter are well known to those skilled in the art. For example, suitable materials include resin beds including zirconium-based resins. Acceptable materials are also described in U.S. Pat. No. 8,647,506 and U.S. Patent Publication No. 2014/0001112. Other acceptable filter materials can be developed and utilized by those skilled in the art without undue experimentation. Depending upon the type of filter material, the filter housing may include a vapor membrane capable of releasing gases such as ammonia.

Preferably, the hemodialysis machine includes two additional flow paths in the form of a "drain" flow path and a "fresh dialysate" flow path. The drain flow path includes one or more fluid drain lines for draining the reservoirs of contaminated dialysate, and the fresh dialysate flow path includes one or more fluid fill lines for transporting fresh dialysate from a supply of fresh dialysate to the reservoirs. One or more fluid pumps may be connected to the drain flow path and/or a fresh dialysate flow path to transport the fluids to their intended destination.

In addition, the hemodialysis machine includes a plurality of fluid valve assemblies for controlling the flow of blood through the blood flow path, for controlling the flow of dialysate through the dialysate flow path, and for controlling the flow of used dialysate through the filter flow path. The valve assemblies may be of any type of electro-mechanical fluid valve construction as can be determined by one skilled in the art including, but not limited to, traditional electro-mechanical two-way fluid valves and three-way fluid valves. A two-way valve is any type of valve with two ports, including an inlet port and an outlet port, wherein the valve simply permits or obstructs the flow of fluid through a fluid pathway. Conversely, a three-way valve possesses three ports and functions to shut off fluid flow in one fluid pathway while opening fluid flow in another pathway. In addition, the dialysis machine's valve assemblies may include safety pinch valves, such as a pinch valve connected to the venous blood line for selectively permitting or obstructing the flow of blood through the venous blood line. The pinch valve is provided so as to pinch the venous blood line and thereby prevent the flow of blood back to the patient in the event that an unsafe condition has been detected.

Preferably, the hemodialysis machine contains sensors for monitoring hemodialysis. To this end, preferably the dialysis machine has at least one flow sensor connected to the dialysate flow path for detecting fluid flow (volumetric and/or velocity) within the dialysate flow path. In addition, it is preferred that the dialysis machine contain one or more pressure sensors for detecting the pressure within the dialysate flow path, or at least an occlusion sensor for detecting whether the dialysate flow path is blocked. Preferably, the dialysis machine also possesses one or more sensors for measuring the pressure and/or fluid flow within the blood flow path. The pressure and flow rate sensors may be separate components, or pressure and flow rate measurements may be made by a single sensor.

Furthermore, it is preferred that the hemodialysis machine include a blood leak detector ("BLD") which monitors the flow of dialysate through the dialysate flow path and detects whether blood has inappropriately diffused through the dialyzer's semipermeable membrane into the dialysate flow path. In a preferred embodiment, the hemodialysis machine includes a blood leak sensor assembly incorporating a light source which emits light through the dialysate flow path and a light sensor which receives the light that has been emitted through the dialysate flow path. After passing through the dialysate flow path, the received light is then analyzed to determine if the light has been altered to reflect possible blood in the dialysate.

The dialysis machine preferably includes additional sensors including an ammonia sensor and a pH sensor for detecting the level of ammonia and pH within the dialysate. Preferably, the ammonia sensor and pH sensor are in the dialysate flow path immediately downstream of the filter. In addition, the dialysis machine possesses a bubble sensor connected to the arterial blood line and a bubble sensor connected to the venous blood line for detecting whether gaseous bubbles have formed in the blood flow path.

The hemodialysis machine possesses a processor containing the dedicated electronics for controlling the hemodialysis system. The hemodialysis machine's processor contains power management and control electrical circuitry connected to the pump motors, valves, and dialysis machine sensors for controlling proper operation of the hemodialysis machine. Furthermore, the hemodialysis machine includes a user interface connected to the processor for enabling a person to control the hemodialysis machine's software and hardware. The user interface may include any electromechanical device enabling a user to interact with the processor such as display screens, keyboards, and/or a mouse. In a preferred embodiment, the user interface is a graphical user interface in the form of a touchscreen. In addition, the hemodialysis machine may include simple electromechanical switches and/or mechanical valves such as for turning on/off the machine, or for manually disabling any of the fluid conduits.

In addition, the hemodialysis system includes a machine for generating dialysate, referred to herein as a dialysate generator. The dialysate generator may utilize any known method and/or apparatus for purifying water such as filtration, sedimentation, and distillation, or a combination of these. In a preferred embodiment, the dialysate generator incorporates a combination of carbon filtration, ultraviolet disinfection, and reverse osmosis (RO) filtration. Furthermore, the dialysate generator includes conduits, providing fluid pathways, which carry water from a water inlet through a variety of filters, valves, heaters, mixers, pumps, ultraviolet disinfecting units, sensors and sources of reagents to produce. The fresh dialysate is expelled from the dialysate generator's outlet directly to one of the hemodialysis machine's reservoirs.

In the preferred embodiment, water enters the dialysate generator through a water inlet. Thereafter, the water is transported through the dialysate generator's flow path which includes an inlet flow path, a main filtration loop, and an outlet flow path. The dialysate generator's inlet flow path, in turn, includes a pressure regulator, one-way valve, a first carbon and sediment filter, a sample port, and a second carbon filter, referred to herein as a carbon polisher. The carbon filtered water is then directed through a main filtration loop including a ultraviolet (UV) disinfector, a water descaler, a temperature sensor, a pressure sensor, a conductivity sensor, a pump (preferably membrane), and an additional pressure sensor, to a reverse osmosis membrane. The reverse osmosis membrane outputs "clean water" and a "reject" effluent. The reject effluent from the reverse osmosis membrane is split by a bypass valve with some of the reject effluent being discarded, and the other part of the reject effluent being sent to a pair of parallel variable fluid restrictor orifices that controllably restrict the flow of water and generate back pressure in the reverse osmosis membrane. Reject effluent can be directed back through a check valve to the beginning of the main filtration loop.

The clean water from the reverse osmosis membrane undergoes further processing and testing. To this end, the clean water is directed through a flowrate meter, heater, temperature sensor, and conductivity sensor. If the tested water is determined to be acceptable for purposes of creating dialysate, concentrated reagents are introduced into the clean water by a pair of pumps to create dialysate. The concentrated reagents may contain one or more of the following: bicarbonate solution, acid solution, lactate solution, and salt solution. Additional conductivity sensors are provided to confirm whether the proper amounts of reagents are being introduced into the water.

Before the dialysate is sent to the hemodialysis machine, the now generated dialysate passes through an additional ultraviolet disinfector to kill any remaining bacteria and a submicron filter to remove any endotoxins that might remain from dead bacteria. The sterilized dialysate is delivered to the hemodialysis machine through the dialysate generator's fluid outlet. Preferably, the dialysate generator possesses a plurality of bypass flow paths and controllable valves to control various functions of the dialysate generator.

In another embodiment of the hemodialysis system, the one or more reservoirs are located in the dialysate generator machine, not in the hemodialysis machine. For this embodiment, the one or more reservoirs are in the dialysate generator machine's flow path to form a closed loop system for transporting dialysate from the one or more reservoirs to the hemodialysis machine and back to the reservoir. More preferably, the dialysate generator possesses two (or more) dialysate reservoirs which can be alternatively placed within the dialysate generator's flow path. When one reservoir possesses contaminated dialysate, dialysis treatment can continue using the other reservoir while the reservoir with contaminated dialysate is emptied and refilled. Like the embodiment wherein the reservoirs are located within the hemodialysis machine, the reservoirs may be of any size as required by clinicians to perform an appropriate hemodialysis treatment. However, it is preferred that the two reservoirs be the same size and sufficiently small so as to enable the dialysis machine to be easily portable. Acceptable reservoirs are 0.5 liters to 5.0 liters in size. The preferred reservoir stores approximately 2.0 liters of dialysate.

The hemodialysis machine and dialysate generator are standalone machines that may connect or disconnect from one another. To this end, preferably the hemodialysis machine includes a housing for encapsulating and protecting the various components which provide hemodialysis treatment. In addition, the hemodialysis machine's housing includes electrical connectors and fluid connectors for connecting to the dialysate generator. Similarly, the dialysate generator includes a housing for encapsulating and protecting the various components which generate fresh dialysate. Also similar to the hemodialysis machine, the dialysate generator's housing includes electrical connectors and fluid connectors for connecting to the hemodialysis machine. More specifically, in addition to the fluid connectors and fluid conduits which transport fresh dialysate to the hemodialysis machine and the fluid conduits and fluid connectors which receive spent dialysate from the hemodialysis machine, the hemodialysis machine and dialysate generator include electrical wiring and engageable (and disengageable) electrical terminals which connect the hemodialysis machine's processor to all of the electrical and electromechanical components of the dialysate generator. These include all of the dialysate generator's pumps, sensors, heaters, ultraviolet disinfectors, variable orifices, and valves so as to enable the hemodialysis machine's processor to control the operation of the dialysate generator. Advantageously, mechanically and electrically connecting the dialysate generator to the hemodialysis machine enables a user of the hemodialysis system to control the operation of both the hemodialysis machine and the dialysate generator using only the hemodialysis machine's user interface.

The hemodialysis machine housing and dialysate generator housing may be constructed in innumerable shapes and sizes so as to physically couple together. However, in the preferred embodiment, the hemodialysis machine has a generally hexahedronal shape, and the size and shape as a medium sized suitcase. Since it has a generally hexahedronal shape, the hemodialysis machine's housing has six sides and preferably includes substantially parallel top and bottom sides, substantially parallel left and right sides, and substantially parallel front and a back sides. Meanwhile, the preferred dialysate generator has a housing which has a generally "L" shaped construction including a horizontally extending base unit constructed to rest upon a surface, and a vertically extending back unit which extends vertically from the back of the base unit. Preferably, the dialysate generator's processor and pumps are located in its base unit, and the dialysate generator's filters and concentrated reagents are located in the back unit. Moreover, it is preferred that the carbon filter and reverse osmosis membrane be located in elongate cylindrical containers that are positioned vertically in the dialysate generator's back unit. Also, preferably, the back unit's back side has an openable back panel enabling a person to access all of the disposable components (including the carbon filter, reverse osmosis membrane and containers of concentrated reagents) so that they can be easily removed and replaced when depleted. The dialysate reservoirs may be located either within the hemodialysis machine or within the dialysate generator's housing.

Moreover, the hemodialysis machine housing and dialysate generator housing are constructed so that the hemodialysis machine can engage and rest upon the dialysate generator's base unit with the hemodialysis machine's back side engaging the dialysate generator's back unit to form a stable combination.

The hemodialysis system (including hemodialysis machine and dialysate generator) is transportable, lightweight, easy to use, patient-friendly and capable of in-home use.

In addition, the hemodialysis system provides an extraordinary amount of control and monitoring not previously provided by hemodialysis systems so as to provide enhanced patient safety.

Other features and advantages of the present invention will be appreciated by those skilled in the art upon reading the Detailed Description, which follows with reference to the Drawings.

DETAILED DESCRIPTION OF THE INVENTION

Figure 1:
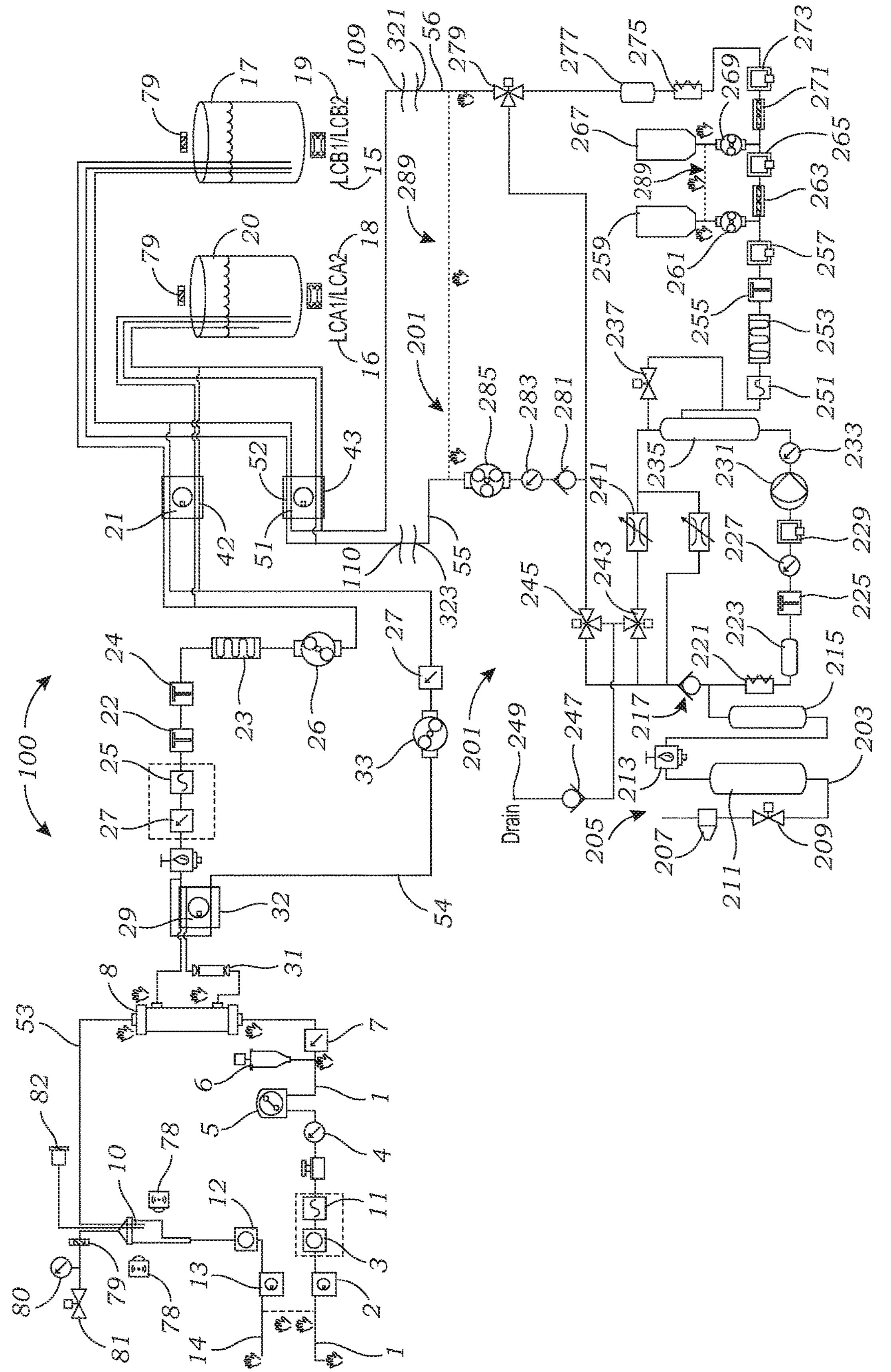
FIG. 1 is a flow chart illustrating the hemodialysis system including the hemodialysis machine.

While the present invention is capable of embodiment in various forms, as shown in the Drawings, hereinafter will describe the presently preferred embodiments of the invention with the understanding that the present disclosure is to be considered as an exemplification of the invention, and it is not intended to limit the invention to the specific embodiments illustrated.

Figure 12:
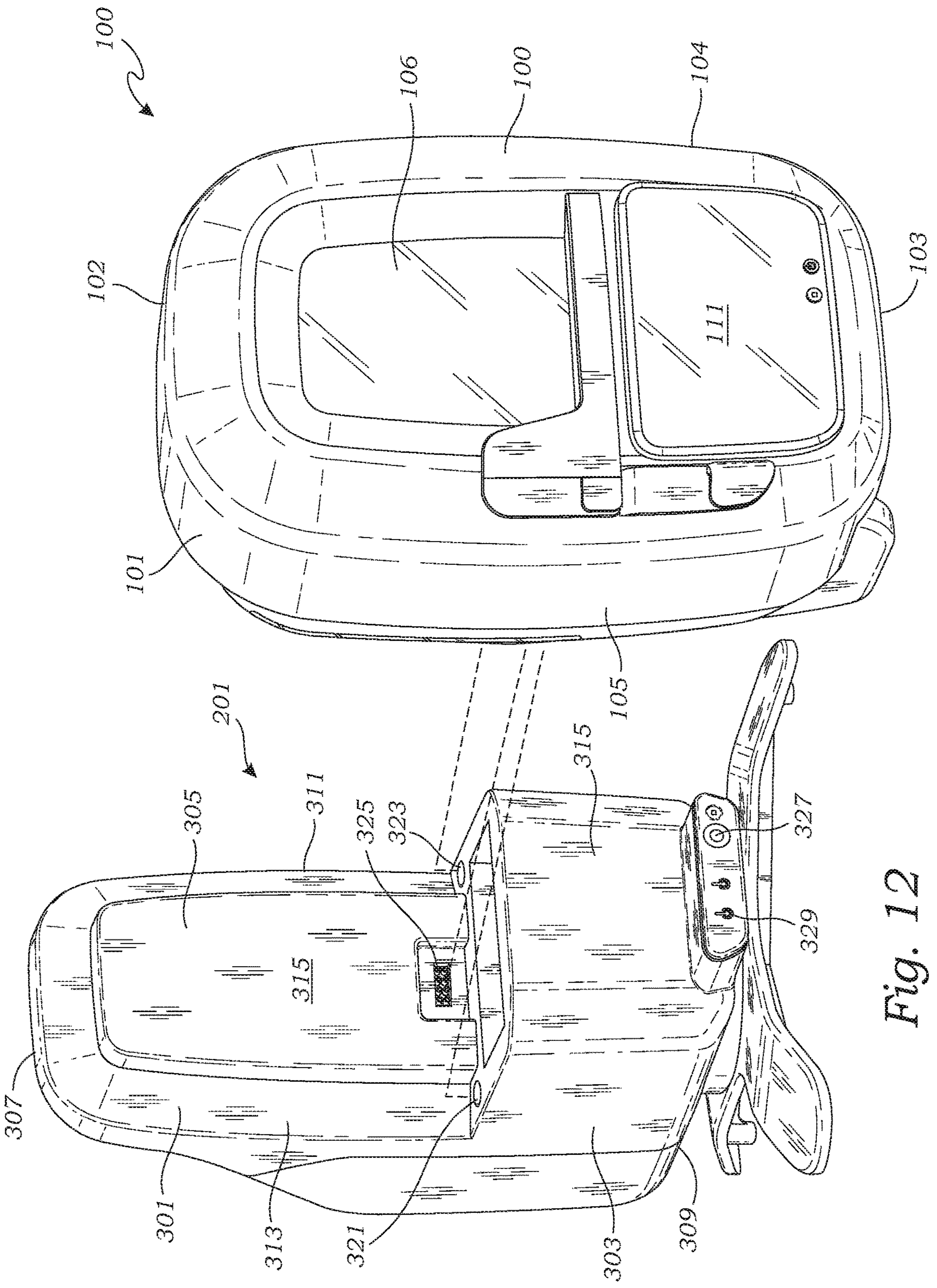
FIG. 12 is an exploded front perspective view of the hemodialysis system.
Figure 13:
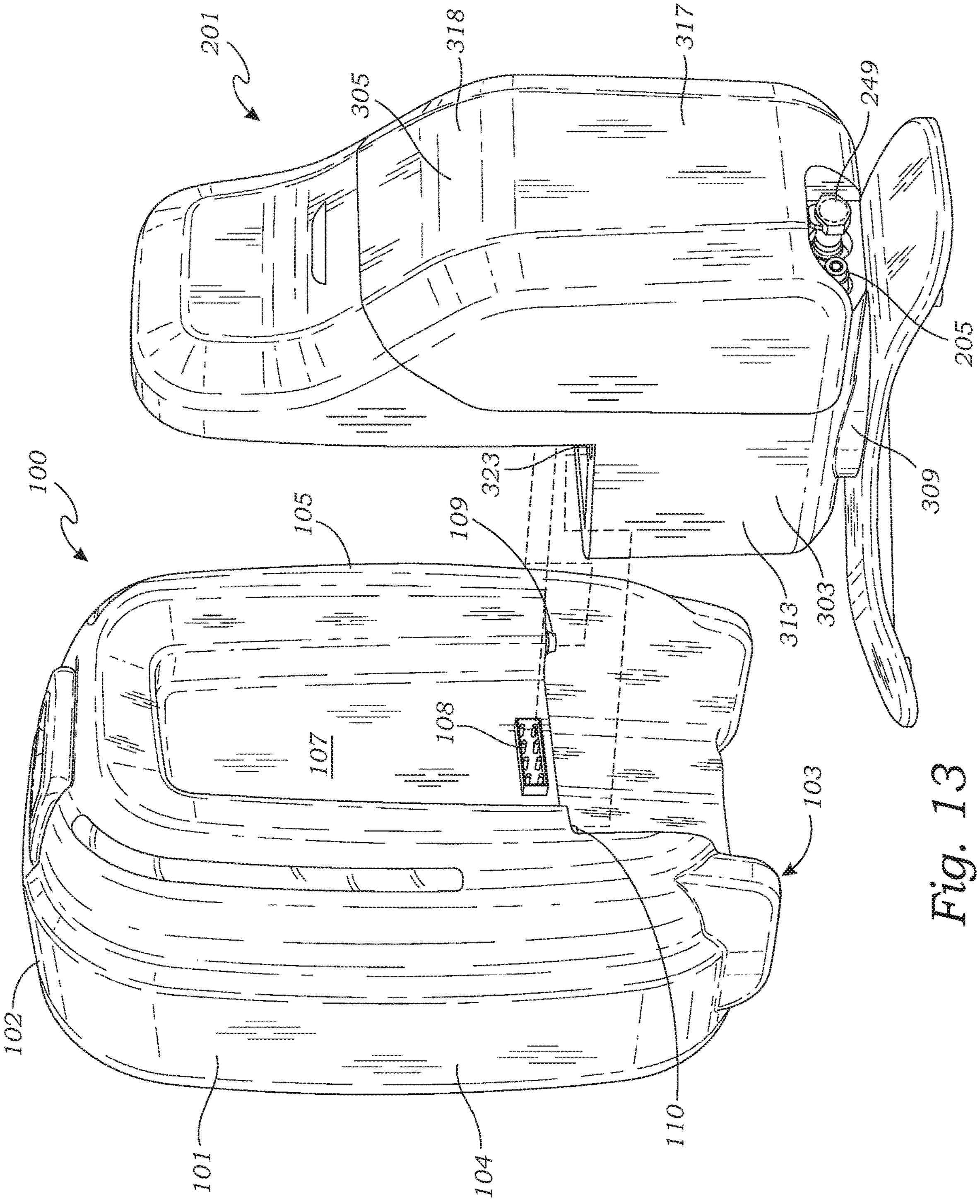
FIG. 13 is an exploded rear perspective view of the hemodialysis system.
Figure 14:
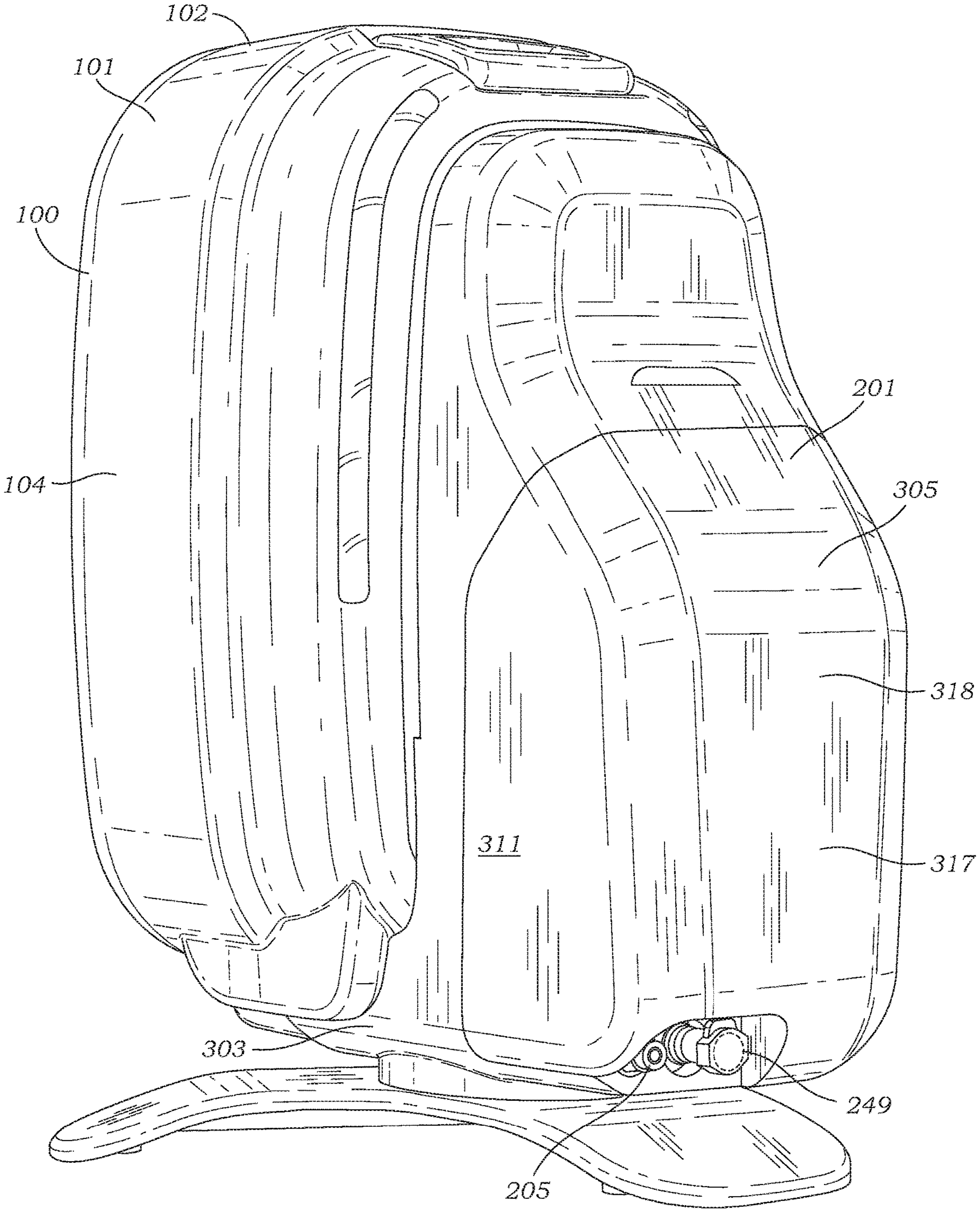
FIG. 14 is a rear perspective view of the hemodialysis system.
Figure 15:
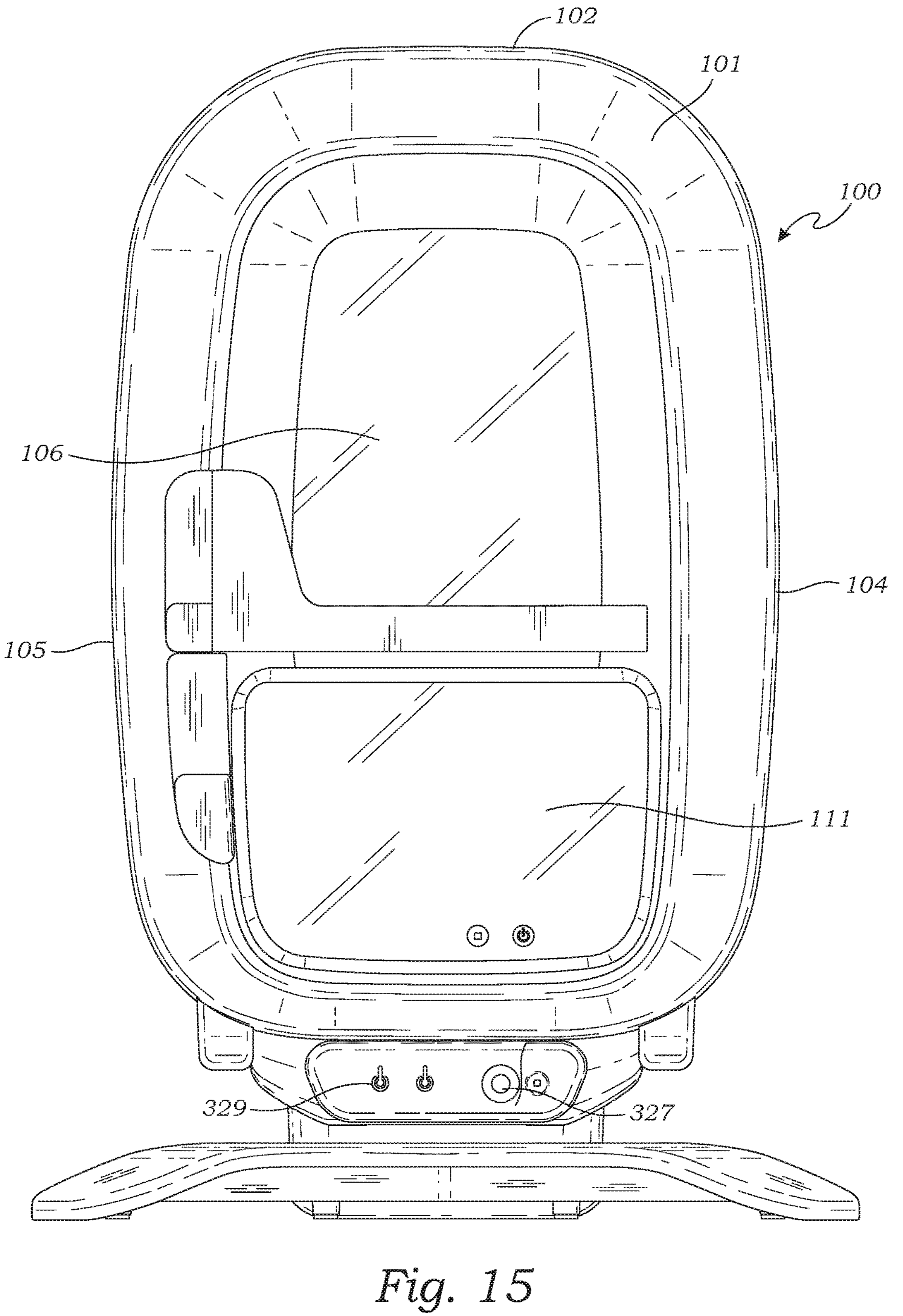
FIG. 15 is a front elevation view of the hemodialysis system.
Figure 16:
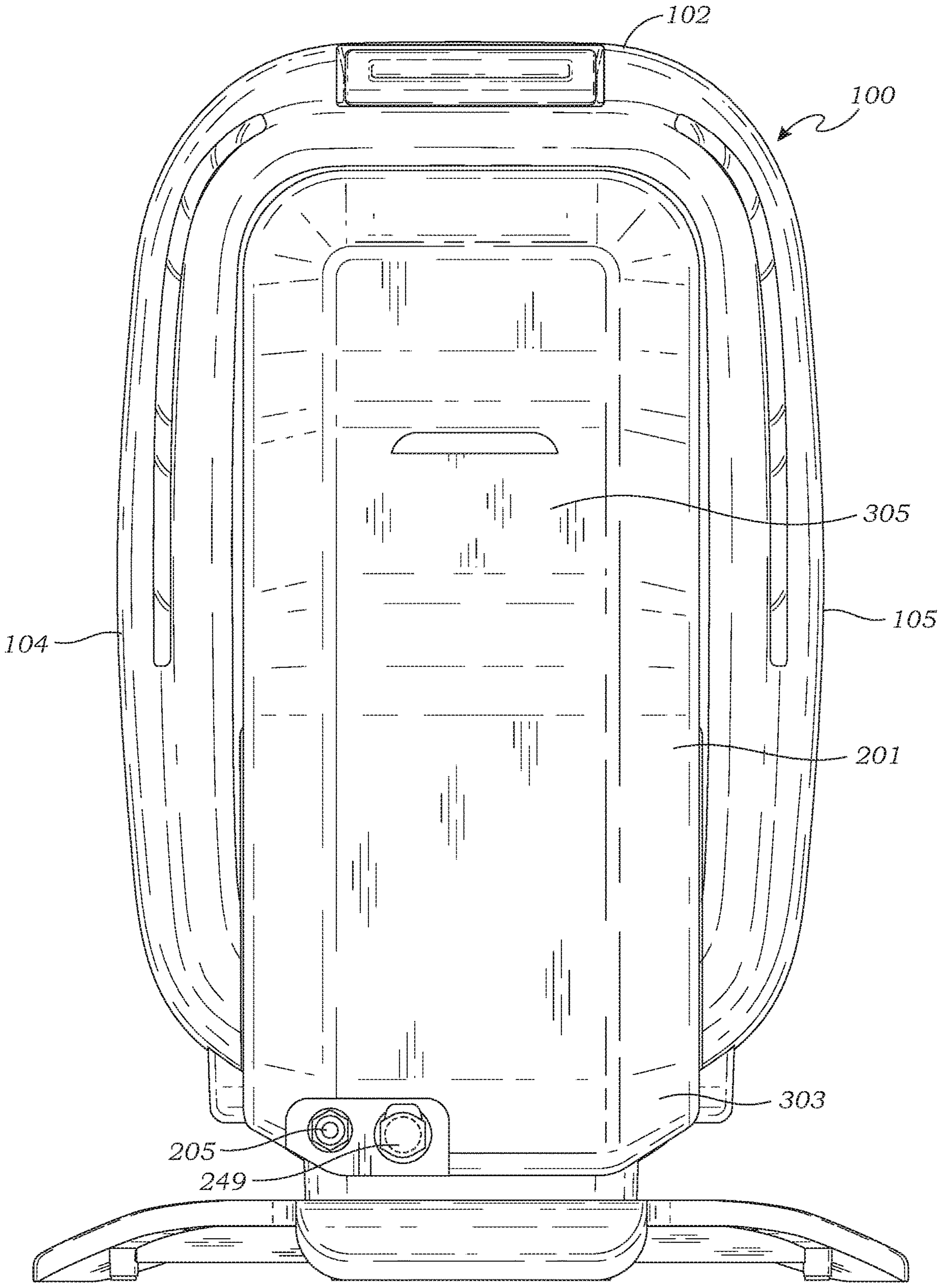
FIG. 16 is a rear elevation view of the hemodialysis system.
Figure 17:
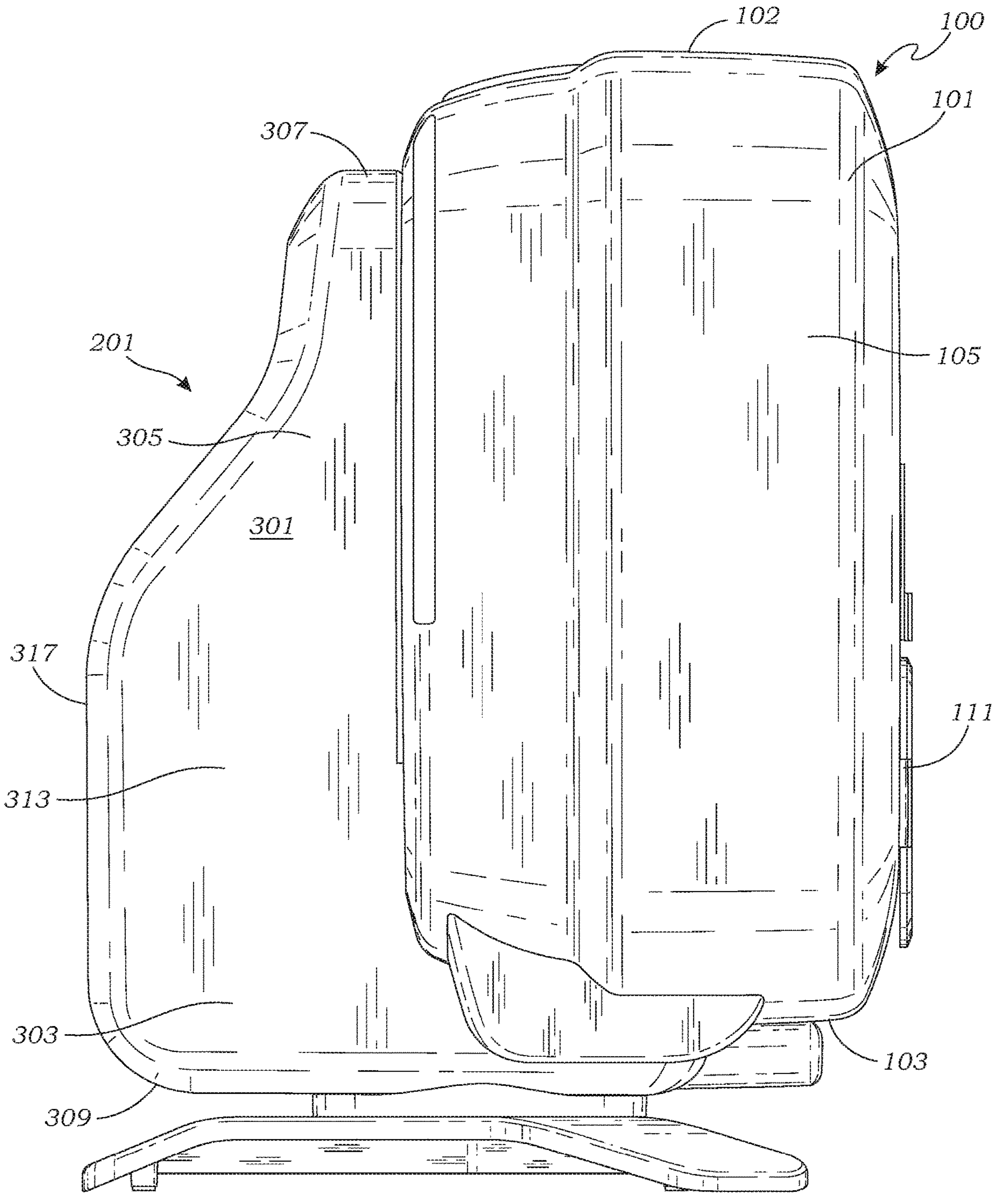
FIG. 17 is a side elevation view of the hemodialysis system.
Figure 18:
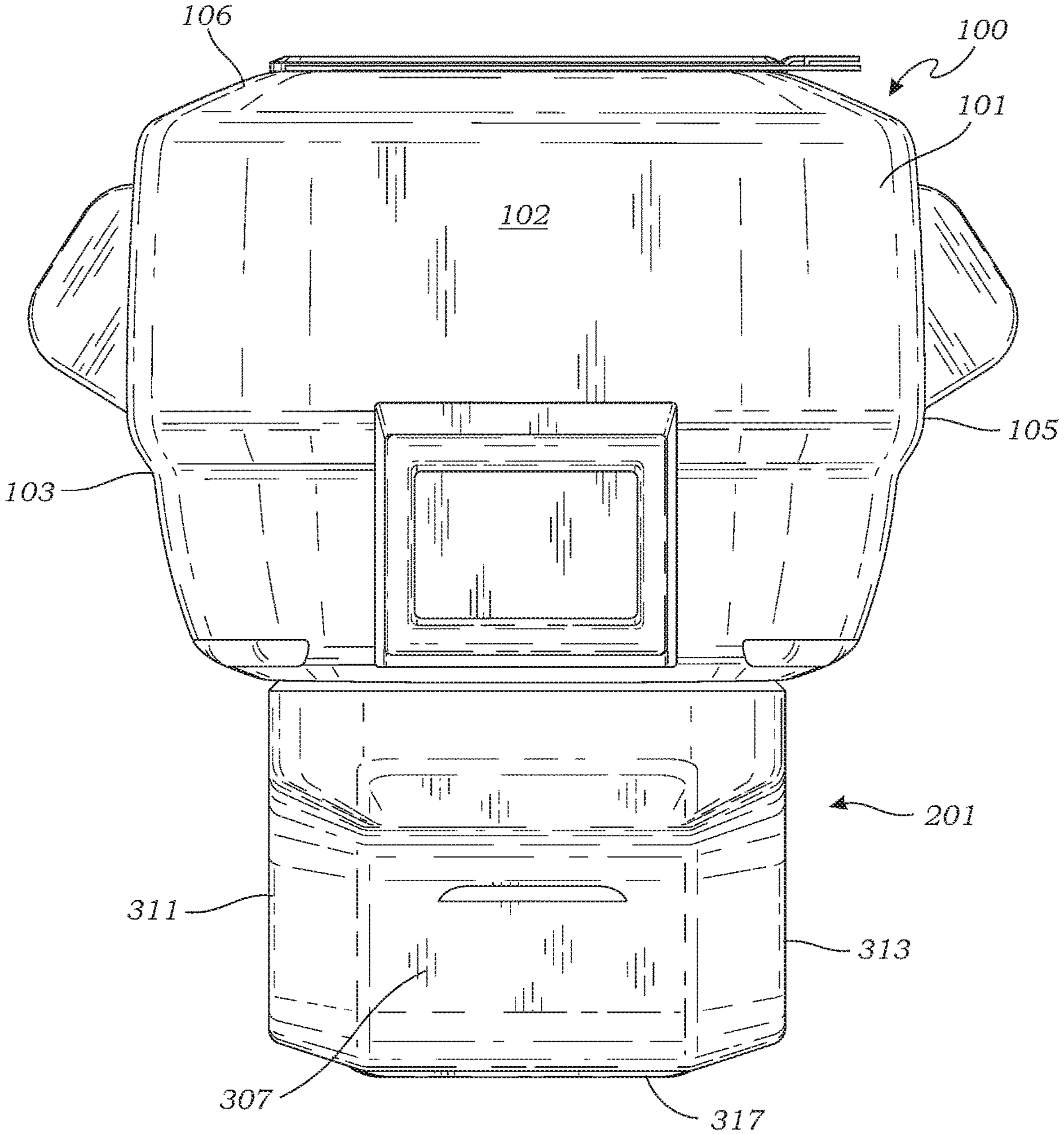
FIG. 18 is a top plan view of the hemodialysis system.
Figure 19:
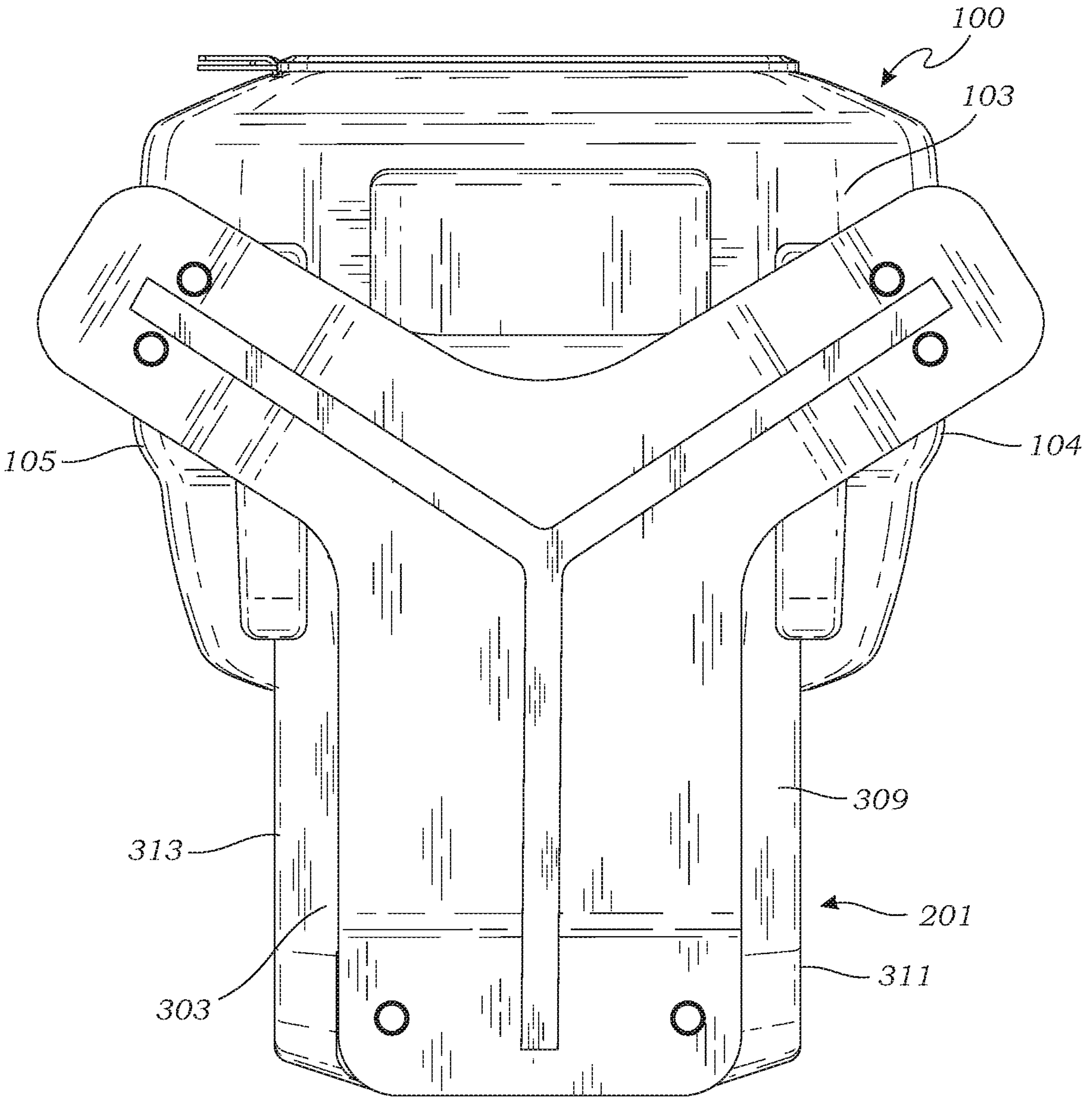
FIG. 19 is a bottom plan view of the hemodialysis system.

As illustrated in FIGS. 1 and 11-19, the hemodialysis system includes a hemodialysis machine 100 and dialysate generator 201 which are physically connectable to and disconnectable from one another. With reference particularly to FIGS. 12 and 13, to connect the hemodialysis machine 100 and dialysate generator 201 together, the hemodialysis machine 100 possesses an electrical connector 108 and fluid connectors 109 and 110, and the dialysate generator 201 possesses an electrical connector 325 and fluid connectors 321 and 323. The respective electoral connectors and fluid connectors are positioned and constructed to allow both a fluid and electrical connection between the two machines. Advantageously, the electrical connectors and fluid connectors are disconnectable to allow one to decouple the dialysate generator from the hemodialysis machine 100.

The Hemodialysis Machine

As best illustrated in FIG. 1, the hemodialysis machine 100 includes a blood flow path 53 and a dialysate flow path 54. The blood flow path 53 includes an arterial blood line 1 for connecting to a patient's artery for collecting blood from a patient, and a venous blood line 14 for connecting to a patient's vein for returning blood to a patient. The arterial blood line 1 and venous blood line 14 may be typical constructions known to those skilled in the art.

The blood flow path 53 transports blood in a closed loop system by connecting to the arterial blood line 1 and venous blood line 14 to a patient for transporting blood from a patient through the dialyzer 8 and back to the patient. Preferably, the hemodialysis machine includes a supply of heparin 6 and a heparin pump connected to the blood flow path 1. The heparin pump delivers small volumes of heparin anticoagulant into the blood flow to reduce the risk of blood clotting in the machine. The heparin pump can take the form of a linearly actuated syringe pump, or the heparin pump may be a bag connected with a small peristaltic or infusion pump.

The hemodialysis machine includes a dialyzer 8 in the dialysate flow path 54 which is of a construction and design known to those skilled in the art. Preferably, the dialyzer 8 includes a large number of hollow fibers which form a semipermeable membrane. Suitable dialyzers can be obtained from Fresenius Medical Care, Baxter International, Inc., Nipro Medical Corporation, and other manufacturers of hollow fiber dialyzers. Both the blood flow path and dialysate flow path travel through the dialyzer 8 which possesses an inlet for receiving dialysate, an outlet for expelling dialysate, an inlet for receiving blood from a patient, and an outlet for returning blood to a patient. Preferably, the dialysate flows in the opposite direction to the blood flowing through the dialyzer with the dialysate flow path isolated from the blood flow path by a semipermeable membrane (not shown). As illustrated in FIGS. 1-6 and as explained in greater detail below, the dialysate flow path 54 transports dialysate in a closed loop system in which dialysate is pumped from a reservoir (17 or 20) to the dialyzer 8 and back to the reservoir (17 or 20). Both the blood flow path 53 and the dialysate flow path 54 pass through the dialyzer 8, but the flow paths are separated by the dialyzer's semipermeable membrane. The reservoirs 17 and 20 may be located within the hemodialysis machine 100, or the reservoirs 17 and 20 may be located external to the hemodialysis machine, such as in the dialysate generator 201.

Preferably, the hemodialysis machine includes three primary pumps (5, 26 & 33) for pumping blood and dialysate. For purposes herein, the term "pump" is meant to refer to both the pump actuator which uses suction or pressure to move a fluid, and the pump motor for mechanically moving the actuator. Suitable pump actuators may include an impeller, piston, diaphragm, the lobes of a lobe pump, screws of a screw pump, rollers or linear moving fingers of a peristaltic pump, or any other mechanical construction for moving fluid as can be determined by those skilled in the art. Meanwhile, the pump's motor is the electromechanical apparatus for moving the actuator. The motor may be connected to the pump actuator by shafts or the like. In a preferred embodiment, the dialysate and/or blood flow through traditional flexible tubing and each of the pump actuators consists of a peristaltic pump mechanism wherein each pump actuator includes a rotor with a number of cams attached to the external circumference of the rotor in the form of "rollers", "shoes", "wipers", or "lobes", which compress the flexible tube. As the rotor turns, the part of the tube under compression is pinched closed (or "occludes") forcing the fluid to be pumped through the tube. Additionally, as the tube opens to its natural state after the passing of the cam, fluid flow is induced through the tube.

The first and second primary pumps (26 & 33) are connected to the dialysate flow path for pumping dialysate through the dialysate flow path from a reservoir (17 or 20) to the dialyzer 8 and back to the reservoir (17 or 20). A first pump 26 is connected to the dialysate flow path "upstream", (meaning prior in the flow path) from the dialyzer 8 while the second pump 33 is connected to the dialysate flow path "downstream" (meaning subsequent in the flow path) from the dialyzer 8. Meanwhile, the hemodialysis machine's third primary pump 6 is connected to the blood flow path. The third pump 6, also referred to as the blood pump, pumps blood from a patient through the arterial blood line, through the dialyzer 8, and through the venous blood line for return to a patient. It is preferred that the third pump 6 be connected to the blood flow path upstream from the dialyzer. The hemodialysis machine may contain more or less than three primary pumps. For example, the dialysate may be pumped through the dialyzer 8 utilizing only a single pump. However, it is preferred that the hemodialysis machine contain two pumps including a first pump 26 upstream from the dialyzer 8 and a second pump 33 downflow from the dialyzer 8.

In one embodiment illustrated in FIG. 1, the hemodialysis machine 100 contains two or more reservoirs (17 & 20) for storing dialysate solution. Both of the reservoirs (17 and 20) may be connected simultaneously to the dialysate flow path 54 to form one large source of dialysate. However, this is not considered preferred. Instead, the hemodialysis system includes a valve assembly 21 for introducing either, but not both, of the two reservoirs (17 or 20) into the dialysate flow path 54 to form a closed loop system for transporting a dialysate from one of the two reservoirs to the dialyzer and back to that reservoir. After the dialysate in a first reservoir 17 has been used, is no longer sufficiently clean, or does not possess appropriate chemical properties, the hemodialysis machine's valve 21 is controlled to remove the first reservoir 17 from the dialysate flow path and substitute the second reservoir 20, which has fresh dialysate, into the dialysate flow path. Thus, when one reservoir possesses contaminated dialysate, and the reservoir needs to be emptied and refilled with freshly generated dialysis fluid 75, dialysis treatment can continue using the other reservoir.

In this manner, the hemodialysis machine may switch between each reservoir 17 and 20 times over the course of the treatment. Furthermore, the presence of two reservoirs as opposed to one reservoir allows for the measurement of the flow rate for pump calibration or ultrafiltration measurement, while isolating the other reservoir while it is being drained or filled. Though the reservoirs may be of any size as required by clinicians to perform an appropriate hemodialysis treatment, preferred reservoirs have a volume between 0.5 liters and 5.0 liters.

For the embodiment illustrated in FIGS. 1-9, the hemodialysis system includes a drain flow path 55 to dispose of waste dialysate from the reservoirs (17 and 20). In the embodiment illustrated in the FIGS. 1-4, the drain flow path 55 is connected to both reservoirs (17 and 20). Waste dialysate may drain through the drain flow path 5 through a gravity feed, or the hemodialysis system may include a pump of any type as can be selected by those skilled in the art to pump used dialysate to be discarded.

With reference still to FIG. 1, the hemodialysis machine preferably possesses a heater 23 thermally connected to the dialysate flow path or to reservoirs for heating the dialysate to a desired temperature. For example, in an embodiment illustrated in FIG. 1, a single heater 23 is thermally coupled to the dialysate flow path downstream of both reservoirs (17 & 20). However, the hemodialysis machine may include additional heaters, and the one or more heaters may be in different locations. For example, in an alternative embodiment, the hemodialysis system includes two heaters, with a single heater thermally coupled to each reservoir. The one or more heaters are preferably activated by electricity and include a resistor which produces heat with the passage of an electric current.

In addition, the hemodialysis machine 100 possesses various sensors for monitoring hemodialysis, and in particular, the blood flow path 53 and dialysate flow path 54. To this end, the hemodialysis machine 100 preferably has one or more flow sensors 25 connected to the dialysate flow path for monitoring fluid flow (volumetric and/or velocity) within the dialysate flow path 54. In addition, it is preferred that the hemodialysis machine contain one or more pressure, or occlusion, sensors (9 & 27) for detecting the pressure within the dialysate flow path. Preferably, the hemodialysis machine also possesses one or more sensors for measuring the pressure (4 & 7) and/or fluid flow 11 within the blood flow path.

Preferably, the hemodialysis machine includes temperature sensors (22, 24 & 28) for measuring the temperature of the dialysate throughout the dialysate flow path. One of the temperature sensors, such as temperature sensor 24, may be a conductivity/temperature sensor. In addition, the hemodialysis system possesses level sensors for detecting the level of fluid in the reservoirs (17 & 20). Preferred level sensors may include either capacitive fluid level sensors, ultrasonic fluid level sensors, or load cells. In a preferred embodiment, the level of each reservoir is measured by a pair of redundant load cells 15, 16, 18, and 19. Furthermore, it is preferred that the hemodialysis machine includes a blood leak detector 31 which monitors the flow of dialysate through the dialysate flow path and detects whether blood has inappropriately diffused through the dialyzer's semipermeable membrane into the dialysate flow path.

Preferably, the hemodialysis machine also contains a first pinch valve 2 connected to the arterial blood line 1 for selectively permitting or obstructing the flow of blood through the arterial blood line, and a second pinch valve 13 connected to the venous blood line 14 for selectively permitting or obstructing the flow of blood through the venous blood line. The pinch valves are provided so as to pinch the arterial blood line 1 and venous blood line 14 to prevent the flow of blood back to the patient in the event that any of the sensors have detected an unsafe condition. Providing still additional safety features, the hemodialysis machine includes blood line bubble sensors (3 & 12) to detect if an air bubble travels backwards down the arterial line (blood leak sensor 3) or venous line (blood leak sensor 12). Further, the blood flow path 53 may include a bubble trap 10 which has a pocket of pressurized air inside a plastic housing. Bubbles rise to the top of the bubble trap, while blood continues to flow to the lower outlet of the trap. This component reduces the risk of bubbles traveling into the patient's blood.

Preferably, the level of fluid in the bubble trap is measured by one or more level sensors 78. Furthermore, in a preferred embodiment, the hemodialysis machine 100 includes an apparatus to increase or decrease the pressure within the bubble trap 10. As illustrated in FIG. 1, the preferred hemodialysis machine 100 includes an air release flow path including a transducer protector 79, a pressure sensor 80, and a variable air release valve 81. The transducer protector 79 allows air to pass, but not fluids, to prevent blood from being released through the air release flow path. The variable air release valve 81 can be opened or closed. When closed, blood moving through the blood flow path 53 will cause the pressure within the blood flow path 53 and bubble trap 10 to increase. This pressure can be controllably reduced (down to ambient pressure) by opening the air release valve 81 to release air through the air release flow path. By adjusting the valve to between a fully open condition and a fully closed condition, the hemodialysis machine can control and maintain the fluid pressure within the blood flow path 53.

To control the flow and direction of blood and dialysate through the hemodialysis system, the hemodialysis system includes a variety of fluid valves for controlling the flow of fluid through the various flow paths of the hemodialysis system. The various valves include pinch valves and 2-way valves which must be opened or closed, and 3-way valves which divert dialysate through a desired flow pathway as intended. In addition to the valves identified above, the hemodialysis system includes a 3-way valve 21 located at the reservoirs' outlets which determines from which reservoir (17 or 20) dialysate passes through the dialyzer 8. An additional 3-way valve 42 determines to which reservoir the used dialysate is sent to. Finally, 2-way valves 51 and 52 (which may be pinch valves) are located at the reservoirs' inlets to permit or obstruct the supply of fresh dialysate to the reservoirs (17 & 20). Of course, alternative valves may be employed as can be determined by those skilled in the art, and the present invention is not intended to be limited the specific 2-way valve or 3-way valve that have been identified.

Though not shown in the Figures, the hemodialysis machine 100 includes a processor and a user interface. The processor contains the dedicated electronics for controlling the hemodialysis system including power management circuitry connected to the pump motors, sensors, valves and heater for controlling proper operation of the hemodialysis machine. The processor monitors each of the various sensors to ensure that hemodialysis treatment is proceeding in accordance with a preprogrammed procedure input by medical personnel into the user interface. The processor may be a general-purpose computer or microprocessor including hardware and software as can be determined by those skilled in the art to monitor the various sensors and provide automated or directed control of the heater, pumps, and pinch valve. The processor may be located within the electronics of a circuit board or within the aggregate processing of multiple circuit boards.

Also not shown, the hemodialysis machine includes a power supply for providing power to the processor, user interface 111, pump motors, valves and sensors. The processor is connected to the dialysis machine sensors (including reservoir level sensors (15 & 18), blood leak sensor 31, pressure and flow rate sensors (4, 7, 9, 11, 25 & 27), temperature/conductivity sensors (22, 24 & 28), blood line bubble sensors (3 & 12), pumps (5, 6, 26, 33, 40, 44, 47 & 49), and pinch valves (2 & 13) by traditional electrical circuitry.

In operation, the processor is electrically connected to the first, second and third primary pumps (5, 26, & 33) for controlling the activation and rotational velocity of the pump motors, which in turn controls the pump actuators, which in turn controls the pressure and fluid velocity of blood through the blood flow path and the pressure and fluid velocity of dialysate through the dialysate flow path. By independently controlling operation of the dialysate pumps 26 and 33, the processor can maintain, increase, or decrease the pressure and/or fluid flow within the dialysate flow path within the dialyzer. Moreover, by controlling all three pumps independently, the processor can control the pressure differential across the dialyzer's semipermeable membrane to maintain a predetermined pressure differential (zero, positive or negative), or maintain a predetermined pressure range. For example, most hemodialysis is performed with a zero or near zero pressure differential across the semipermeable membrane, and to this end, the processor can monitor and control the pumps to maintain this desired zero or near zero pressure differential. Alternatively, the processor may monitor the pressure sensors and control the pump motors, and in turn pump actuators, to increase and maintain positive pressure in the blood flow path within the dialyzer relative to the pressure of the dialysate flow path within the dialyzer. Advantageously, this pressure differential can be affected by the processor to provide ultrafiltration and the transfer of free water and dissolved solutes from the blood to the dialysate.

In the preferred embodiment, the processor monitors the blood flow sensor 11 to control the blood pump flowrate. It uses the dialysate flow sensor 25 to control the dialysate flow rate from the upstream dialysate pump. The processor then uses the reservoir level sensors (15, 16, 18 & 19) to control the flowrate from the downstream dialysate pump 33. The change in fluid level (or volume) in the dialysate reservoir is identical to the change in volume of the patient. By monitoring and controlling the level in the reservoir, forward, reverse, or zero ultrafiltration can be accomplished.

Moreover, the processor monitors all of the various sensors to ensure that the hemodialysis machine is operating efficiently and safely, and in the event that an unsafe or non-specified condition is detected, the processor corrects the deficiency or ceases further hemodialysis treatment. For example, if the venous blood line pressure sensor 9 indicates an unsafe pressure or the bubble sensor 12 detects a gaseous bubble in the venous blood line, the processor signals an alarm, the pumps are deactivated, and the pinch valves are closed to prevent further blood flow back to the patient. Similarly, if the blood leak sensor 31 detects that blood has permeated the dialyzer's semipermeable membrane, the processor signals an alarm and ceases further hemodialysis treatment.

The dialysis machine's user interface may include a keyboard or touchscreen 111 for enabling a patient or medical personnel to input commands concerning treatment or enable a patient or medical personnel to monitor performance of the hemodialysis machine. Moreover, the processor may include Wi-Fi or Bluetooth connectivity for the transfer of information or control to a remote location.

Hereinafter will be identified the various components of the preferred hemodialysis machine with the numbers corresponding to the components illustrated in the Figures.

| | |
|---|---|
| 1 | Arterial tubing connection |
| 2 | Pinch valve, arterial line. Used to shut off the flow connection with the patient, in case of an identified warning state potentially harmful to the patient. |
| 3 | Bubble sensor, arterial line |
| 4 | Pressure sensor, blood pump inlet |
| 5 | Blood pump |
| 6 | Heparin supply and pump |
| 7 | Pressure sensor, dialyzer input |
| 8 | Dialyzer |
| 9 | Pressure sensor, dialyzer output |
| 10 | Bubble trap |
| 11 | Flow sensor, blood Circuit |
| 12 | Bubble sensor, venous line |
| 13 | Pinch valve, venous line |
| 14 | Venous tubing connection |
| 15 | Primary level sensor, first reservoir |
| 16 | Secondary level sensor, first reservoir |
| 17 | First reservoir which holds dialysis fluid |
| 18 | Primary level sensor, second reservoir |
| 19 | Secondary level sensor, second reservoir |
| 20 | Second reservoir which holds dialysis fluid |
| 21 | 3-way valve, reservoir outlet. |
| 22 | Temperature sensor, heater inlet. |
| 23 | Fluid heater for heating the dialysis fluid from approximately room temperature or tap temperature, up to the human body temperature of 37° C. |
| 24 | Combined conductivity and temperature sensor |
| 25 | Flow sensor, Dialysis Circuit |
| 26 | Dialysis pump, dialyzer inlet |
| 27 | Pressure sensor, Dialysis Circuit |
| 28 | Temperature sensor, dialyzer inlet |
| 29 | 3-way valve, dialyzer inlet |
| 31 | Blood leak detector |
| 32 | 3-way valve, dialyzer outlet |
| 33 | Dialysis pump, dialyzer outlet |
| 42 | 3-way valve, reservoir recirculation. |
| 43 | 3-way valve, reservoir drain. |
| 44 | Pump, reservoir drain. |
| 51 | Pinch valve, first reservoir inlet. |
| 52 | Pinch valve, second reservoir inlet. |
| 53 | Blood flow path |

-continued

| | |
|---|---|
| 54 | Dialysate flow path |
| 55 | Drain flow path |
| 56 | Fresh dialysis flow path |
| 78 | Level sensor |
| 79 | transducer protector |
| 80 | Pressure sensor |
| 81 | Vent valve |
| 82 | Injection port |
| 100 | Hemodialysis machine |
| 101 | Housing |
| 102 | Top |
| 103 | Bottom |
| 104 | Left |
| 105 | Right |
| 106 | Front |
| 107 | Back |
| 108 | Electrical connector |
| 109 | Fluid connector |
| 110 | Fluid connector |
| 111 | Touchscreen (graphical user interface) |

Hemodialysis Treatment Options

The hemodialysis system provides increased flexibility of treatment options based on the required frequency of dialysis, the characteristics of the patient, the availability of dialysate or water and the desired portability of the dialysis machine. For all treatments, the blood flow path 53 transports blood in a closed loop system by connecting to the arterial blood line 1 and venous blood line 14 to a patient for transporting blood from a patient to the dialyzer and back to the patient.

With reference to FIG. 1, a first method of providing hemodialysis includes the step of introducing dialysate to the hemodialysis machine through the fresh dialysate flow path 56 from a water supply 46 such as water supplied through reverse osmosis (RO). The mixed dialysate is then introduced to reservoirs 17 and 20. For this treatment, the dialysate from a first reservoir is recirculated past the dialyzer 8 through bypass path 35 back to the same reservoir. When the volume of the reservoir has been recirculated once, the reservoir is emptied through the drain flow path 55 and the reservoir is refilled through the fresh dialysate flow path 56.

Meanwhile, while the first reservoir is being emptied and refilled, hemodialysis treatment continues using the second reservoir (17 or 20). Once the processor has determined that all dialysate has recirculated once, or determined that the dialysate is contaminated, the processor switches all pertinent valves (21, 42, 43, 51 and 52) to remove the first reservoir 20 from patient treatment, and inserts the second reservoir 17 into the dialysate flow path 54. The dialysate from the second reservoir 17 is recirculated past the dialyzer 8 through bypass path 35 and back to the same reservoir 17. This switching back and forth between reservoirs 17 and 20 continues until the dialysis treatment is complete. This operation is similar, but not the same, as traditional single-pass systems because no sorbent filter is used.

Figure 4:
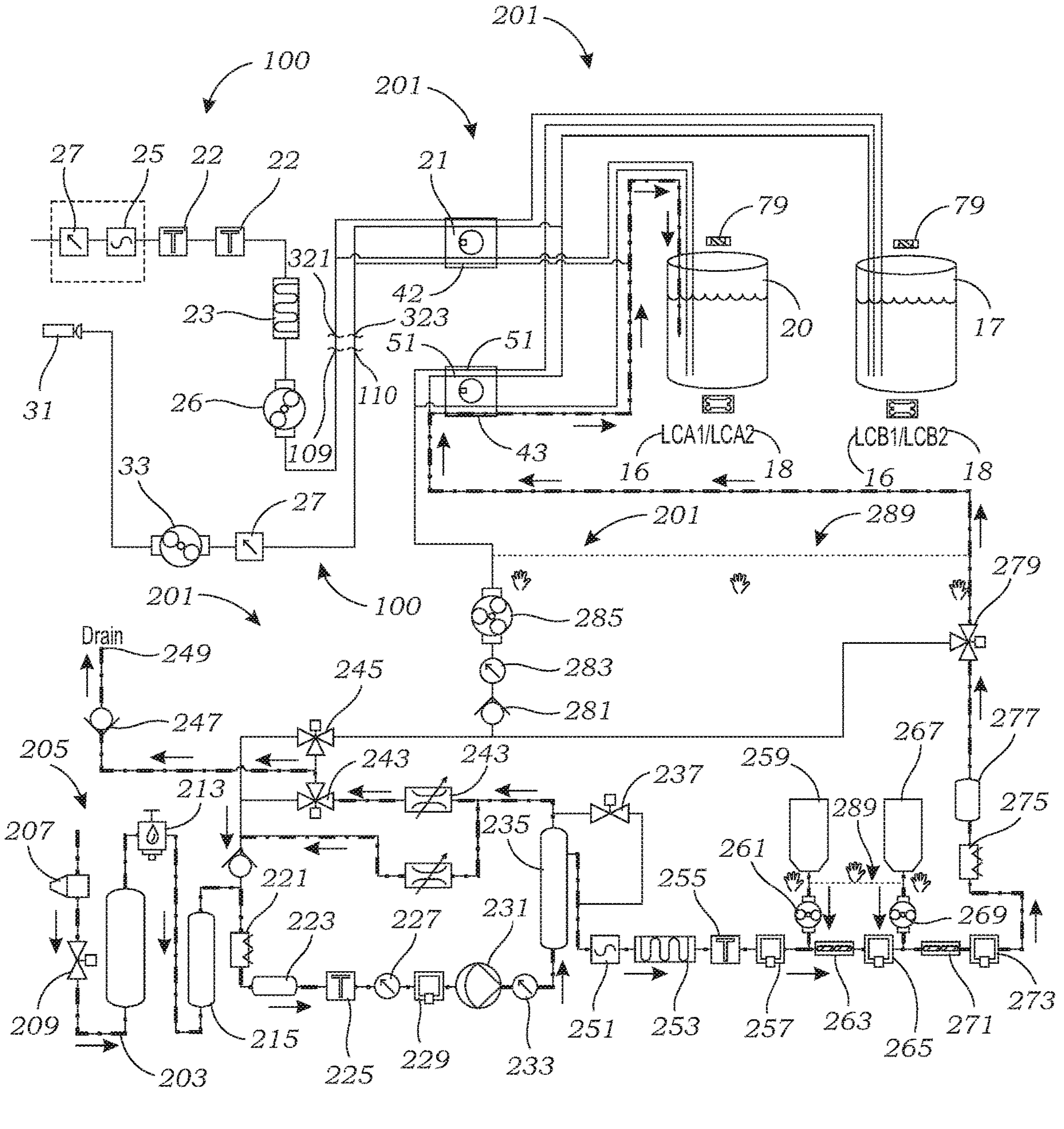
FIG. 4 is the flow chart illustrating the dialysate generator delivering dialysate to the hemodialysis machine, wherein thicker dashed lines illustrate water capable of moving in the flow path.

As illustrated in FIG. 4, once the processor has determined that continued use of reservoir 17 for dialysis treatment is not appropriate, the processor switches the various valve assemblies (21, 42, 43, 51 and 52) to remove reservoir 17 from the dialysate flow path 54, and to instead insert reservoir 20 within the dialysis flow path for dialysis treatment. Clean dialysate is recirculated through the dialyzer 8 back to the same reservoir 20. Again, this recirculation continues using reservoir 20, as determined by the processor, until switching back to reservoir 17, or until dialysis treatment has been completed. While dialysis treatment continues using reservoir 20, contaminated fluid in reservoir 17 is drained through the drain flow path. Thereafter, reservoir 17 is refilled using the fresh dialysate flow path 56. Like other treatment methods, this switching back and forth between reservoirs 17 and 20 continues until the dialysis treatment is complete.

In still an additional embodiment, during treatment, the dialysate 75 from the first reservoir is recirculated past the dialyzer 8 and directed back to the same reservoir. Like the prior embodiments, dialysis treatment is implemented while switching back and forth between reservoirs 17 and 20. While dialysis treatment uses the clean dialysate in reservoir 17, the various valve assemblies (21, 42, 43, 51 and 52) are switched to insert the second reservoir 20 into the closed loop filter flow path 55 and 56. The contaminated water is drained from the reservoir 20.

With reference to FIG. 1, the processor continues to monitor the output of the various sensors including those within the dialysate flow path 54. Once the water within reservoir 17 has become contaminated, it is removed from the dialysate flow path and reservoir 20 is substituted in its place by once again switching all of the pertinent valve assemblies (21, 42, 43, 51 and 52). The dialysate 75 from the second reservoir 20 is recirculated in the closed loop dialysate flow path 54 past the dialyzer 8 and directed back to the same reservoir. Meanwhile, the now contaminated water in reservoir 17 is drained and fresh dialysate is introduced into reservoir 17.

The Dialysate Generator

With reference to FIGS. 1-10, the preferred dialysate generator 201 includes an inlet 205 for introducing water, such as tap water, into the various fluid flow paths of the system. The inlet flow path 203 includes a pressure regulator 207, a one-way valve 209, a first carbon and sediment filter 211, a sample port 213, and a second carbon filter 215. The pressure regulator 207 ensures that the water pressure is not high for the dialysate generator. The first carbon and sediment filter 211 removes sediment, chlorine and chloramines, while the second carbon filter 215 serves as a backup to the upflow filter 211. The filtered water is then directed to a second fluid pathway which includes a ultraviolet (UV) disinfector 221, a water descaler 223, a temperature sensor 225, a pressure sensor 227, a conductivity sensor 229, a pump 231 which is preferably a membrane pump, and an additional pressure sensor 233. The ultraviolet (UV) disinfector kills any bacteria that has entered the system. The descaler removes dissolved calcium from the water. The temperature sensor 225, pressure sensor 227, and conductivity sensor 229 ensure the incoming water meets certain requirements for temperature (TPi), pressure (PPi) and conductivity (CPi). After passing the pressure sensor 233, the water is travels to a reverse osmosis membrane 235.

The ultraviolet disinfector 221 may include any UV light producing light source capable of killing bacteria. In preferred embodiments, the ultraviolet disinfector 221 is a short fluid conduit incorporating UV light producing LEDs with strong short-wavelength (250-280 nm) radiation. Suitable fluid conduits incorporating LEDs can be purchased from Acuva Technologies Inc. and Crystal IS, Inc. The descaler 223 may be any construction for reducing or eliminating the accumulation of calcium scale which results from dissolved calcium carbonate or other calcium salts within the water. Preferably, the descaler does not employ the introduction of chemicals to provide water softening. Instead, the preferred descaler 223 is a mechanical device which provides a drop in water pressure and magnetic fields provided by stationary magnets to convert the dissolved calcium salts into calcium crystals. The calcium crystals may then be removed from the water by a filter located within the descaler, or more preferably by a separate downstream filter within the dialysate generator. A suitable descaler is sold by Dime Water, Inc. of Vista, Calif. and is described in U.S. Pat. No. 6,221,245 which is incorporated by reference in its entirety herein.

The reverse osmosis membrane 235 outputs "clean water" and a "reject" effluent. The reject effluent from the reverse osmosis membrane is split by a bypass valve 237 with some of the reject effluent being discarded, and the other part of the reject effluent being sent to a pair of parallel fluid restrictor orifices 239 and 241 that controllably restrict the flow of water and generate back pressure in the reverse osmosis membrane. These restrictor orifices 239 are constructed to balance the flows through and past the membrane. Some of the water that flows past the reverse osmosis membrane 235 must be discarded through three-way valve 243. Alternatively, some of the water is recirculated through three-way valve 245. A check valve 219 ensures that recirculated water enters the flow path with the inlet water, and not vice.

If fluid is pushed through the reverse osmosis membrane 235, the resulting clean water from undergoes further processing and testing. To this end, the fluid flowrate is measured by flowrate meter 251. The water is heated up to body temperature by a heater 253 with a temperature sensor 255 provided to control the heater 253. The water's conductivity is measured by conductivity sensor 257 to ensure that the reverse osmosis membrane has sufficiently cleaned the water. If the tested water is determined to be acceptable, two chemical concentrates 259 & 267 are added to the water in order to make the final dialysate composition. The concentrated reagents are introduced into the clean water by a pair of pumps 261 and 269 to create the dialysate. Preferably, the pumps 261 and 269 are piston pumps that meter in the chemical concentrates into the stream of pure water. Again, the water's conductivity is measured by conductivity sensors 265 and 273 to ensure that the reverse osmosis membrane 235 has sufficiently cleaned the water, and to confirm that the proper amounts of chemical reagents 259 and 267 have been introduced into the water. Finally, the dialysate is sent past another ultraviolet (UV) disinfector 275 to kill any remaining bacteria, and a submicron ultrafilter 277 then catches any endotoxins that remain from dead bacteria. The sterilized dialysate is delivered to the hemodialysis machine from the dialysate generator's fluid outlet to the hemodialysis machine's fresh dialysate flow path 56.

Preferably, the dialysate generator 201 possesses a plurality of bypass flow paths 289, controllable valves 209, 237, 243, 245 and 279, and pumps 231, 261, 267 and 285 to control various operations of the machine. For example, as illustrated in FIGS. 1-10, preferably the dialysate generator 201 includes a pump 285, a pressure sensor 283 and a check valve 281 connected to the hemodialysis machine's drain flow path 55 for controlling the draining of waste dialysate from the reservoirs 17 or 20. The reservoirs 17 and 20 may be located in either the hemodialysis machine 100 or the dialysate generator 201. However, in the preferred embodiment illustrated in FIGS. 4 and 5, the reservoirs 17 and 20 are located in the dialysate generator 201, as are the control valves 21, 42, 43, and 51. Furthermore, preferably the dialysate generator 201 possesses an additional three-way valve 279 which diverts dialysate from the fresh dialysate flow path 56 back through three-way valve 245 to the drain line 249. In addition, with reference to FIGS. 1 through 10, preferably the dialysate generator 201 possesses a bypass flow path 289 which connects the hemodialysis machine's fresh dialysate flow path 56 with the hemodialysis machine's waste dialysate flow path 55.

The hemodialysis system includes at least one processor containing power management and control electrical circuitry connected to the pump motors, valves, and sensors for controlling proper operation of the hemodialysis system, including the hemodialysis machine and the dialysate generator. The preferred hemodialysis system includes two processors with a first processor located in the hemodialysis machine 100 and a secondary processor located in the dialysate generator 201. However, it is preferred that the primary control processor for the entire hemodialysis system be located in the hemodialysis machine 100, and as described below, preferably the dialysate generator 201 is electrically connected to, and controlled by, this primary processor within the hemodialysis machine 100. However, it is preferred that the dialysate generator 201 include a secondary processor for controlling and cycling through various cleaning and disinfecting modes, but preferably the dialysate generator includes only a single on-off button 327. The preferred dialysate generator 201 does not include any additional buttons, knobs, switches or other control interfaces. Instead, preferably the dialysate generator 201 is controlled exclusively through the hemodialysis machine's user interface 111, or in the event that the dialysate generator is disconnected from hemodialysis machine, the dialysate generator's only function is to cycle through cleaning and disinfecting modes. Preferably, the dialysate generator is provided with one or more status or warning lights that may indicate a fault condition or a requirement to replace a disposable item such as a filter or consumable concentrate. In a preferred embodiment, the dialysate generator 201 includes only a single LED light 329 that provides three different colors to indicate powered, cleaning mode, or error detected.

Preferably, the hemodialysis machine 100 is capable of operating without the dialysate generator 201, such as by obtaining dialysate from a source other than the dialysate generator described herein. However, since the preferred dialysate generator 201 does not have a user interface, other than operating in cleaning mode, the preferred dialysate generator is constructed to operate only with the hemodialysis machine 100 described herein.

Hereinafter will be identified the various components of the preferred dialysate generator with the numbers corresponding to the components illustrated in the Figures.

| | |
|---|---|
| 201 | Dialysate generator |
| 203 | Flow path entry |
| 205 | Water inlet |
| 207 | Pressure regulating valve (PRV) |
| 209 | Inlet valve (VPi) |
| 211 | Carbon filter |
| 213 | Sample port (SPTi) |
| 215 | Carbon polisher |
| 217 | Check valve |
| 219 | Main loop flow path |
| 221 | Ultraviolet light (UVi) |
| 223 | Water descaler |
| 225 | Temperature sensor |
| 227 | Pressure sensor |
| 229 | Conductivity sensor |
| 231 | Pump (RO) |
| 233 | Pressure sensor (PPo) |
| 235 | Reverse osmosis membrane |
| 237 | Bypass valve |
| 239 | Variable orifice 1 |
| 241 | Variable orifice 2 |
| 243 | Valve - three way V8 |

-continued

| | |
|---|---|
| 245 | Valve - three way V5 |
| 247 | Check valve |
| 249 | Drain |
| 251 | Flowrate meter (FMP) |
| 253 | Heater (HP) |
| 255 | Temperature sensor (TPo) |
| 257 | Conductivity (CPo) |
| 259 | Salts |
| 261 | Pump (PLP2) |
| 263 | Mixer (MX2) |
| 265 | Conductivity sensor (CD1) |
| 267 | Bicarbonate/Lactate |
| 269 | Pump (PCP1) |
| 271 | Mixer (MX1) |
| 273 | Conductivity sensor (CD2) |
| 275 | Ultraviolet out (CD2) |
| 277 | Submicron ultra filter (SMF) |
| 279 | Valve - three way (VPo) |
| 281 | Check valve (CVD) |
| 283 | Pressure sensor (PDr) |
| 285 | Drain pump (DRP) |
| 287 | Bypass |
| 289 | Bypass |
| 301 | Housing |
| 303 | Base unit |
| 305 | Back unit |
| 307 | Top |
| 309 | Bottom |
| 311 | Left side |
| 313 | Right side |
| 315 | Front side |
| 317 | Back side |
| 318 | Removable back panel |
| 319 | Resting surface |
| 321 | Fluid connector |
| 323 | Fluid connector |
| 325 | Electrical connector |
| 327 | On-off button |
| 329 | LED indicator |

Dialysate Generator Operations

The dialysate generator can perform various operations. In a first mode illustrated in FIG. 2, the inlet water source is examined to determine whether it meets quality requirements and requirements relating to temperature, pressure and conductivity. The product water is heated to the target dialysate temperature and the water is examined by the various sensors. This mode requires that the valves, heater, pumps, and ultraviolet disinfectors be activated as follows.

| Actuator FIG. No. | Preferred Actuator Type | Actuator State |
|---|---|---|
| 209 -VPi | 1-Way | Open |
| 237 - VBf | 1-Way | Closed |
| 279 - VPo | 3-Way | Recirculate |
| 245 - V5 | 3-Way | to Drain |
| 243 - V8 | 3-Way | to Drain |
| 253 - HP | Heater | On |
| 231 - ROP | Diaphragm | On |
| 269 - PCP1 | Piston | Idle |
| 261 - PCP2 | Piston | Idle |
| 285 - DRP | Gear | Idle |
| 221 - UVi | UV Reactor | On |
| 275 - UVo | UV Reactor | On |

Figure 2:
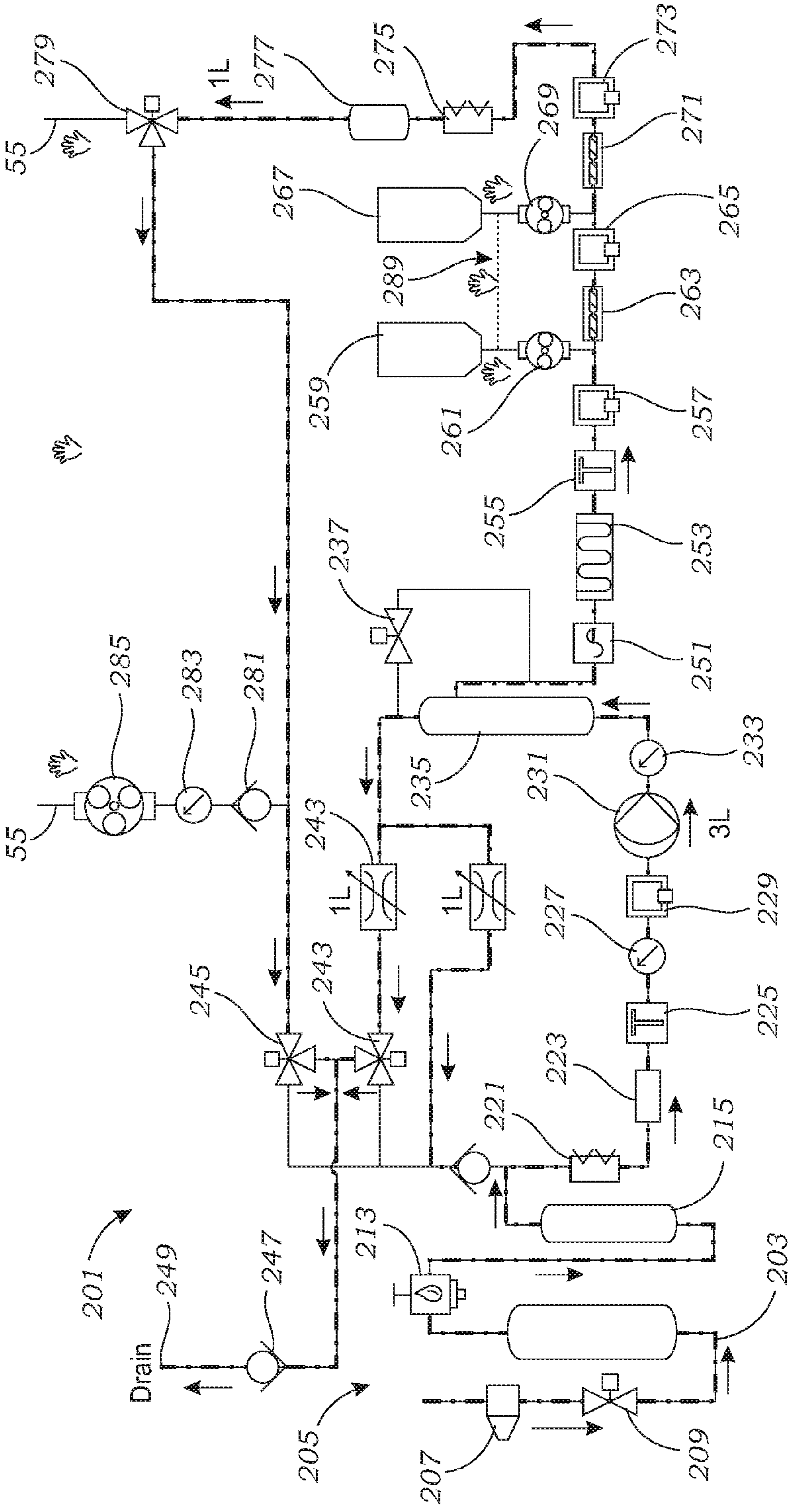
FIG. 2 is the flow chart illustrating the dialysate generator checking its inlet water, wherein thicker dashed lines illustrate water capable of moving in the flow path.

In a second mode illustrated in FIG. 2, the dialysate generator 201 produces clean water, but not dialysate, for the monitoring of reverse osmosis product water. It also heats the water produced by reverse osmosis to the target dialysate treatment temperature and tests the water for temperature compliance. This mode requires that the valves, heater, pumps, and ultraviolet disinfectors be activated as follows.

| Actuator FIG. No. | Preferred Actuator Type | Actuator State |
|---|---|---|
| 209 -VPi | 1-Way | Open |
| 237 - VBf | 1-Way | Closed |
| 279 - VPo | 3-Way | Recirculate |
| 245 - V5 | 3-Way | to Drain |
| 243 - V8 | 3-Way | to Drain |
| 253 - HP | Heater | On |
| 231 - ROP | Diaphragm | On |
| 269 - PCP1 | Piston | Idle |
| 261 - PCP2 | Piston | Idle |
| 285 - DRP | Gear | Idle |
| 221 - UVi | UV Reactor | On |
| 275 - UVo | UV Reactor | On |

Figure 3:
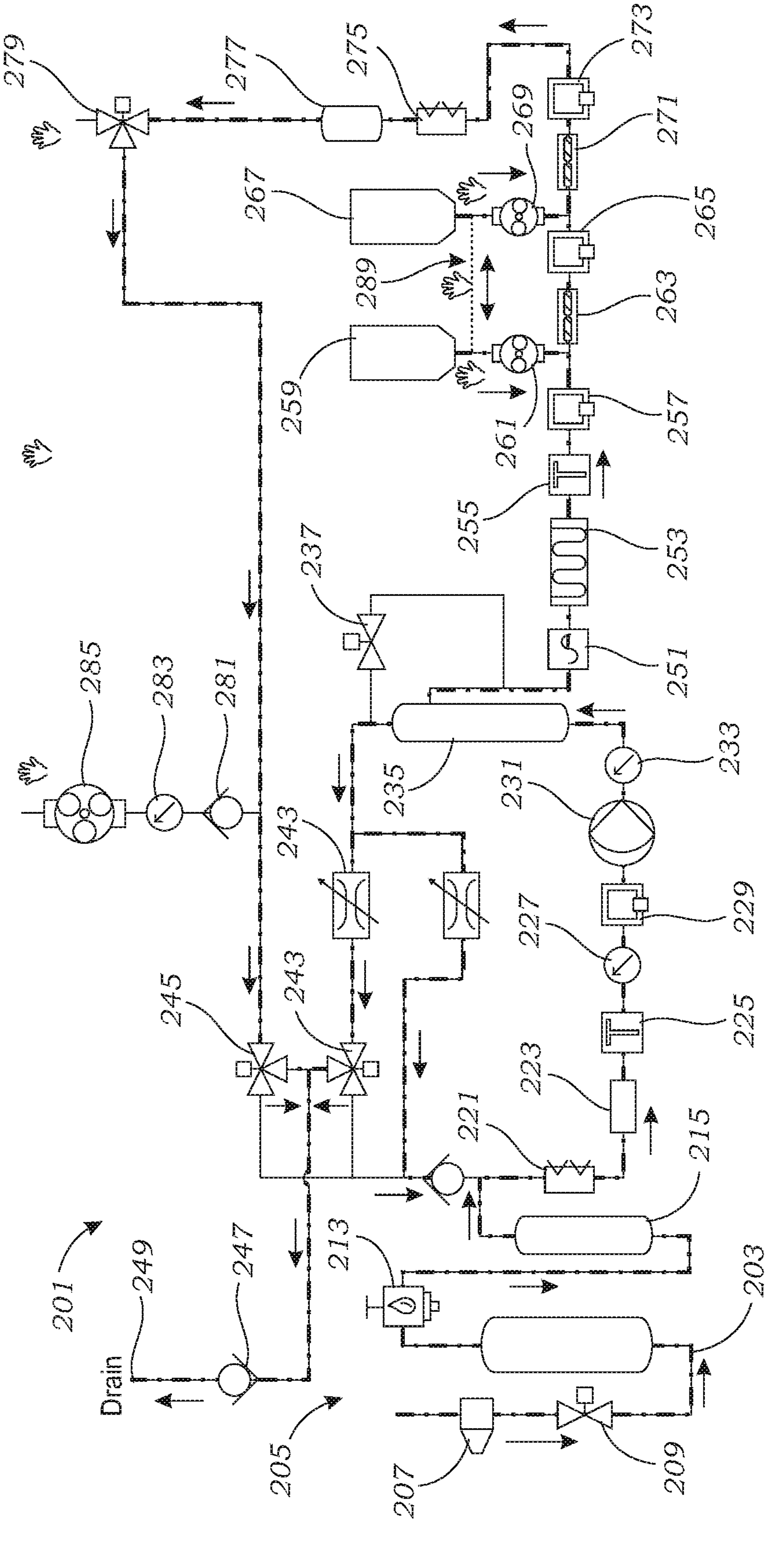
FIG. 3 is the flow chart illustrating the dialysate generator producing dialysate, wherein thicker dashed lines illustrate water capable of moving in the flow path.

In a third mode illustrated in FIG. 3, the dialysate generator 201 generates dialysate. Chemical concentrates are added to reverse osmosis created clean water to create the correct composition of dialysate. However, the dialysate is not provided to the hemodialysis machine 100. Instead, the dialysate is tested to confirm it meets quality requirements. This mode requires that the valves, heater, pumps, and ultraviolet disinfectors be activated as follows.

| Actuator FIG. No. | Preferred Actuator Type | Actuator State |
|---|---|---|
| 209 -VPi | 1-Way | Open |
| 237 - VBf | 1-Way | Closed |
| 279 - VPo | 3-Way | Recirculate |
| 245 - V5 | 3-Way | to Drain |
| 243 - V8 | 3-Way | to Drain |
| 253 - HP | Heater | On |
| 231 - ROP | Diaphragm | On |
| 269 - PCP1 | Piston | On |
| 261 - PCP2 | Piston | On |
| 285 - DRP | Gear | Idle |
| 221 - UVi | UV Reactor | On |
| 275 - UVo | UV Reactor | On |

In a fourth mode illustrated in FIG. 4, the dialysate generator 201 generates dialysate and delivers the dialysate to the hemodialysis machine. The hemodialysis machine diverts the created dialysate to one reservoir of the other (17 or 20). This mode requires that the valves, heater, pumps, and ultraviolet disinfectors be activated as follows.

| Actuator FIG. No. | Preferred Actuator Type | Actuator State |
|---|---|---|
| 209 -VPi | 1-Way | Open |
| 237 - VBf | 1-Way | Closed |
| 279 - VPo | 3-Way | Deliver |
| 245 - V5 | 3-Way | to Drain |
| 243 - V8 | 3-Way | to Drain |
| 253 - HP | Heater | On |
| 231 - ROP | Diaphragm | On |
| 269 - PCP1 | Piston | On |
| 261 - PCP2 | Piston | On |
| 285 - DRP | Gear | Idle |
| 221 - UVi | UV Reactor | On |
| 275 - UVo | UV Reactor | On |

Figure 5:
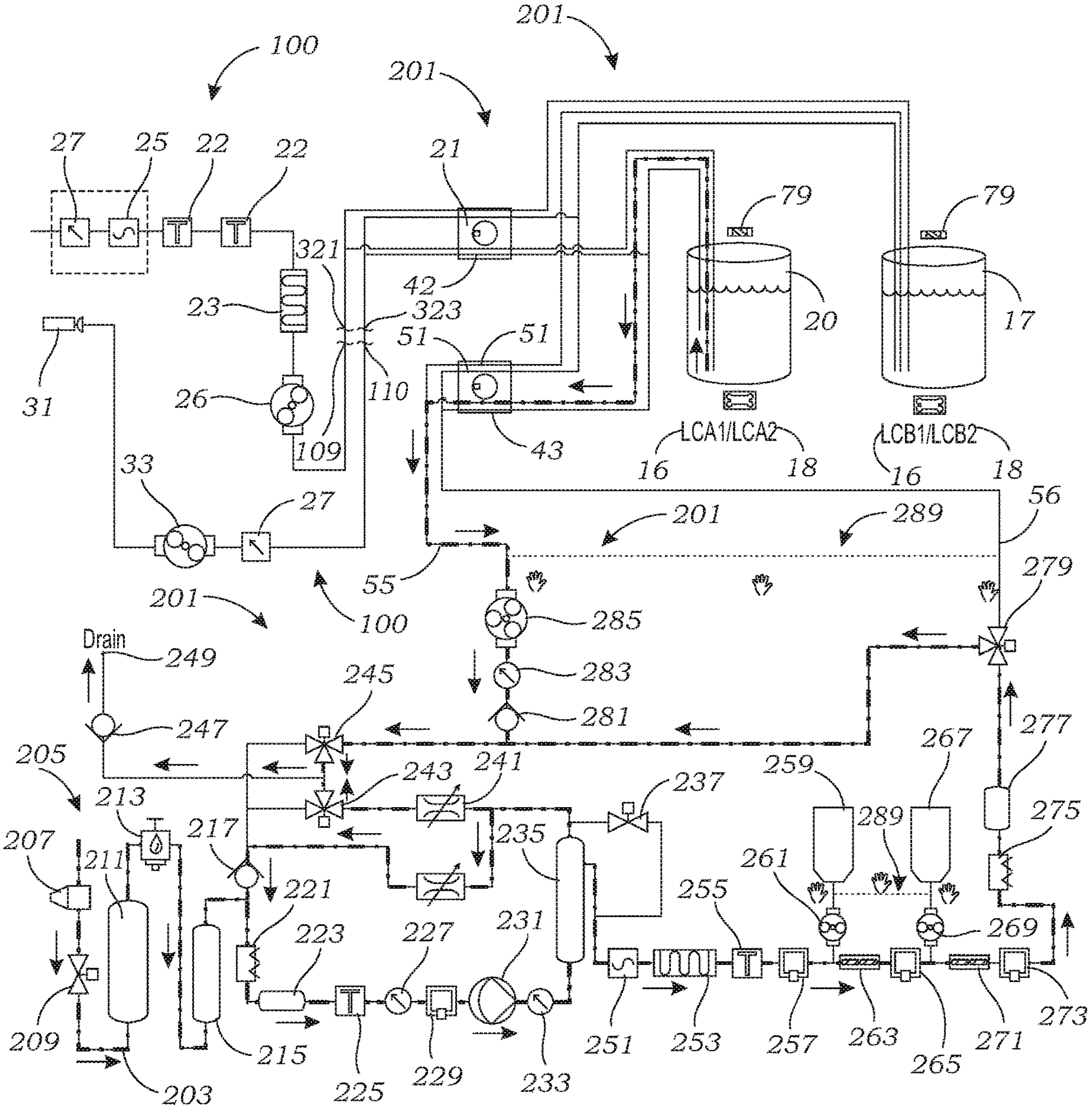
FIG. 5 is the flow chart illustrating the dialysate generator draining dialysate from the hemodialysis machine wherein thicker dashed lines illustrate water capable of moving in the flow path.

In a fifth mode illustrated in FIG. 5, the dialysate generator 201 drains waste dialysate from one of the hemodialysis reservoirs (17 or 20). While dialysate is being drained, no new dialysate is being created and the additional chemical concentrates stop. The hemodialysis machine determines which reservoir to drain, which as illustrated in FIG. 5 is reservoir 20. This mode requires that the valves, heater, pumps, and ultraviolet disinfectors be activated as follows.

| Actuator FIG. No. | Preferred Actuator Type | Actuator State |
|---|---|---|
| 209 -VPi | 1-Way | Open |
| 237 - VBf | 1-Way | Closed |
| 279 - VPo | 3-Way | Recirculate |
| 245 - V5 | 3-Way | to Drain |
| 243 - V8 | 3-Way | to Drain |
| 253 - HP | Heater | On |
| 231 - ROP | Diaphragm | On |
| 269 - PCP1 | Piston | Idle |
| 261 - PCP2 | Piston | Idle |
| 285 - DRP | Gear | On |
| 221 - UVi | UV Reactor | On |
| 275 - UVo | UV Reactor | On |

Figure 6:
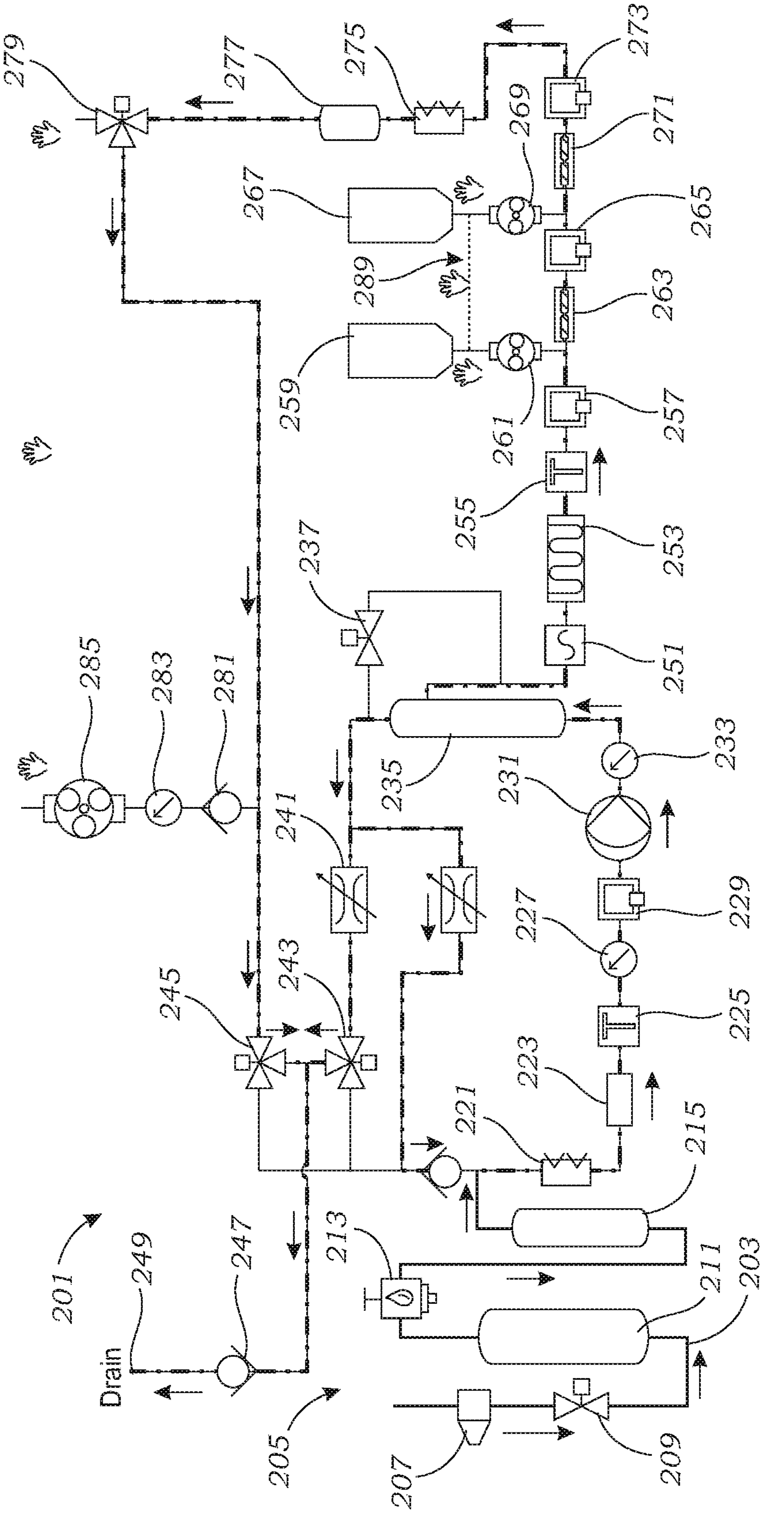
FIG. 6 is the flow chart illustrating the dialysate generator flushing dialysate from the dialysate generator using fresh water, wherein thicker dashed lines illustrate water capable of moving in the flow path.

In a sixth mode illustrated in FIG. 6, the dialysate generator 201 flushes dialysate from its fluid pathways. This mode requires that the valves, heater, pumps, and ultraviolet disinfectors be activated as follows.

| Actuator FIG. No. | Preferred Actuator Type | Actuator State |
|---|---|---|
| 209 -VPi | 1-Way | Open |
| 237 - VBf | 1-Way | Closed |
| 279 - VPo | 3-Way | Recirculate |
| 245 - V5 | 3-Way | to Drain |
| 243 - V8 | 3-Way | to Drain |
| 253 - HP | Heater | On |
| 231 - ROP | Diaphragm | On |
| 269 - PCP1 | Piston | Idle |
| 261 - PCP2 | Piston | Idle |
| 285 - DRP | Gear | Idle |
| 221 - UVi | UV Reactor | On |
| 275 - UVo | UV Reactor | On |

In additional modes, the dialysate generator 201 disinfects itself. The disinfection activates the heater 253 to heat the water in the system up to 85° C. The water is recirculated through the various flow paths of the system. The different paths are alternated and balanced so that the entire system is uniformly heated. Occasionally fluid will be directed to drain to disinfect the lines to the drain. As fluid is directed to drain, new fluid is pulled into the system. During disinfection valve 237—VBf is opened to prevent high pressure across the reverse osmosis membrane.

Figure 7:
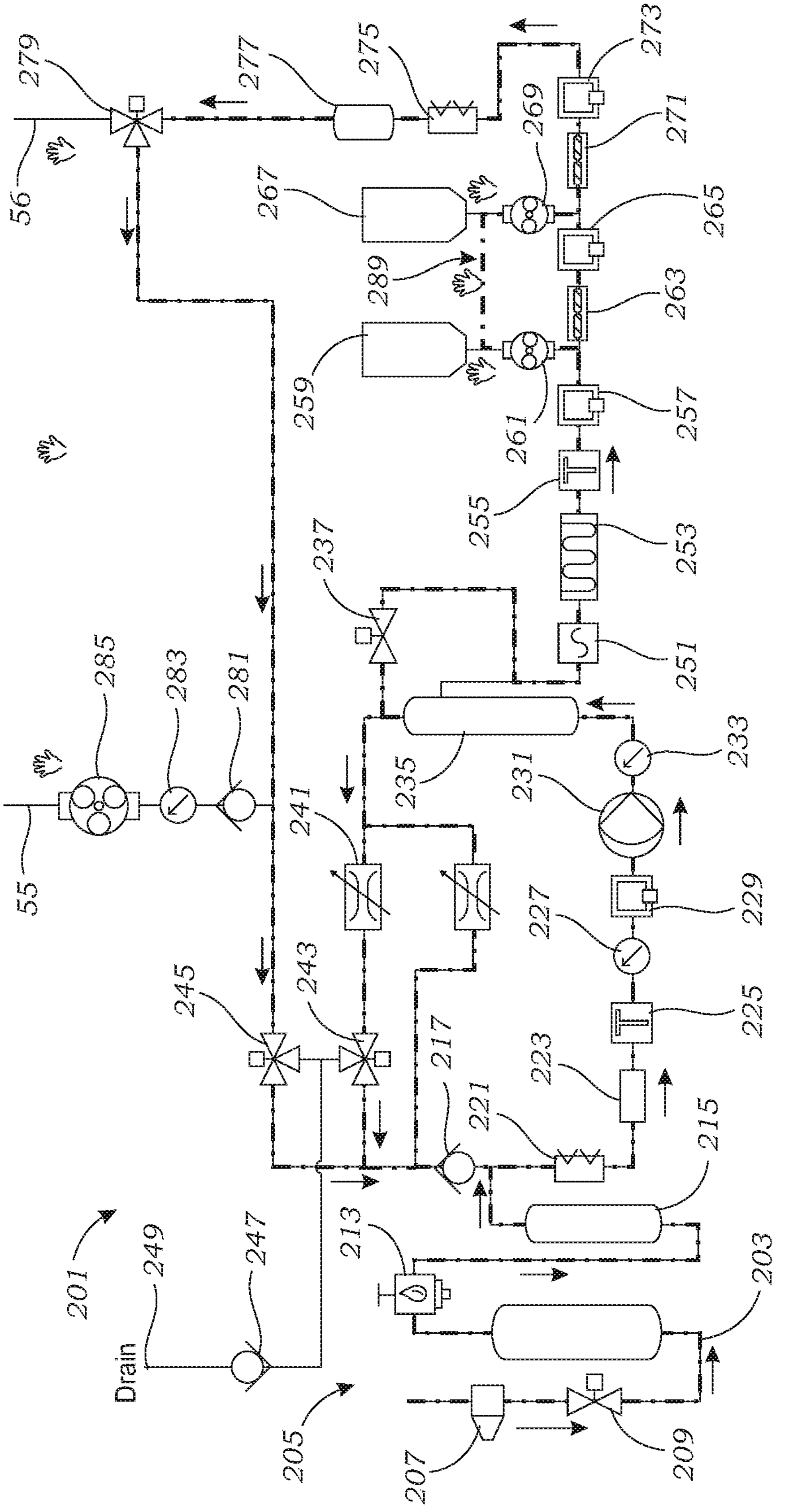
FIG. 7 is the flow chart illustrating the dialysate generator disinfecting itself with hot water, wherein thicker dashed lines illustrate water capable of moving in the flow path.

In a first disinfecting mode illustrated in FIG. 7, hot water is recirculated throughout its fluidic pathways to disinfect the system. This mode requires that the valves, heater, pumps, and ultraviolet disinfectors be activated as follows.

| Actuator FIG. No. | Preferred Actuator Type | Actuator State |
|---|---|---|
| 209 -VPi | 1-Way | Open |
| 237 - VBf | 1-Way | Open |
| 279 - VPo | 3-Way | Recirculate |
| 245 - V5 | 3-Way | Recirculate |
| 243 - V8 | 3-Way | Recirculate |
| 253 - HP | Heater | On |
| 231 - ROP | Diaphragm | On |
| 269 - PCP1 | Piston | On |
| 261 - PCP2 | Piston | On |
| 285 - DRP | Gear | Idle |
| 221 - UVi | UV Reactor | Off |
| 275 - UVo | UV Reactor | Off |

Figure 8:
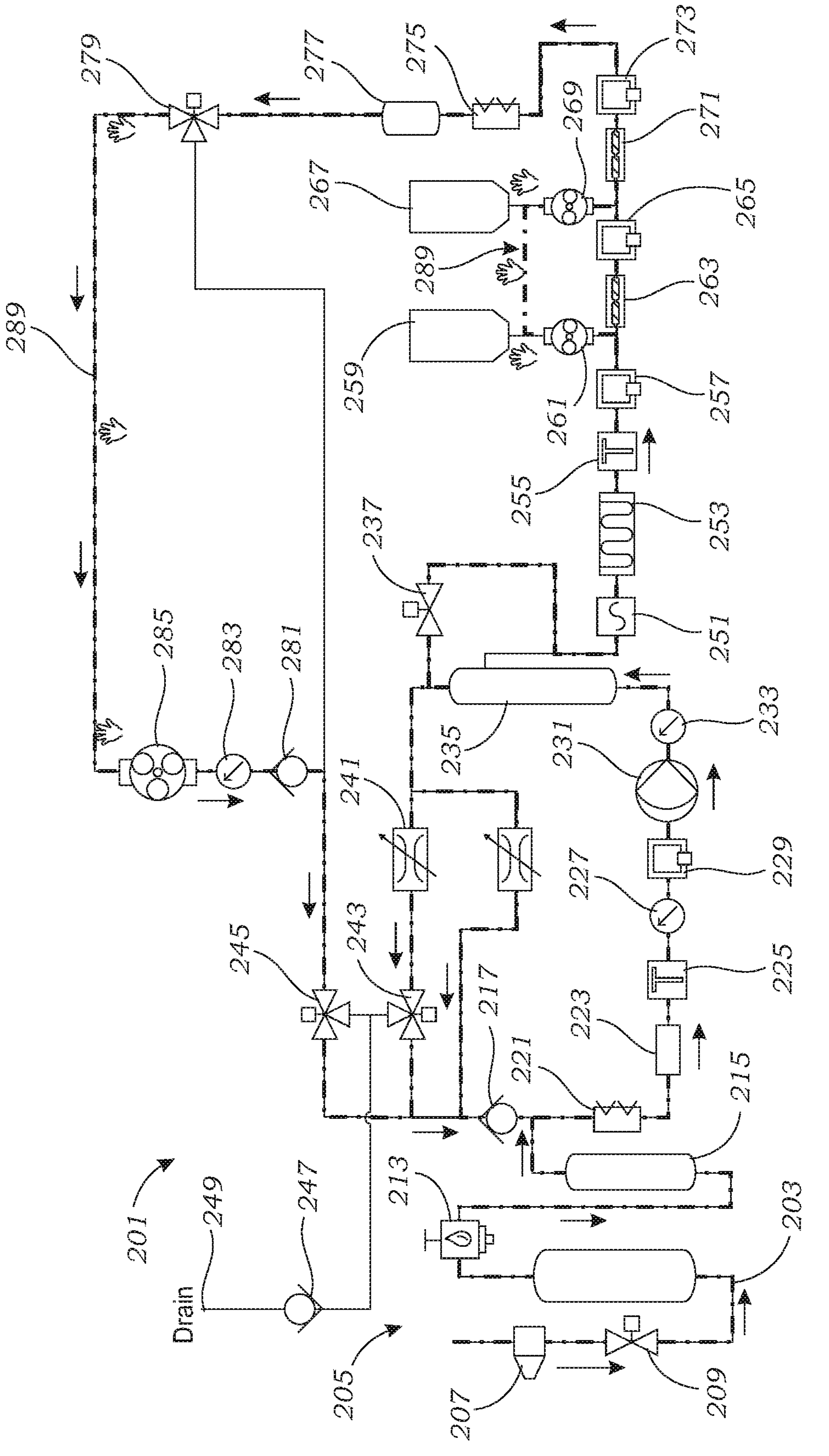
FIG. 8 is the flow chart illustrating the dialysate generator disinfecting the waste fluid pathway from the hemodialysis machine, wherein thicker dashed lines illustrate water capable of moving in the flow path.

In a second disinfecting mode, the dialysate generator 201 disinfects the "waste" fluid pathway by recirculating hot water through selected pathways, as illustrated in FIG. 8. This mode requires that the valves, heater, pumps, and ultraviolet disinfectors be activated as follows.

| Actuator FIG. No. | Preferred Actuator Type | Actuator State |
|---|---|---|
| 209 -VPi | 1-Way | Open |
| 237 - VBf | 1-Way | Open |
| 279 - VPo | 3-Way | Deliver |
| 245 - V5 | 3-Way | Recirculate |
| 243 - V8 | 3-Way | Recirculate |
| 253 - HP | Heater | On |
| 231 - ROP | Diaphragm | On |
| 269 - PCP1 | Piston | On |
| 261 - PCP2 | Piston | On |
| 285 - DRP | Gear | On |
| 221 - UVi | UV Reactor | Off |
| 275 - UVo | UV Reactor | Off |

Figure 9:
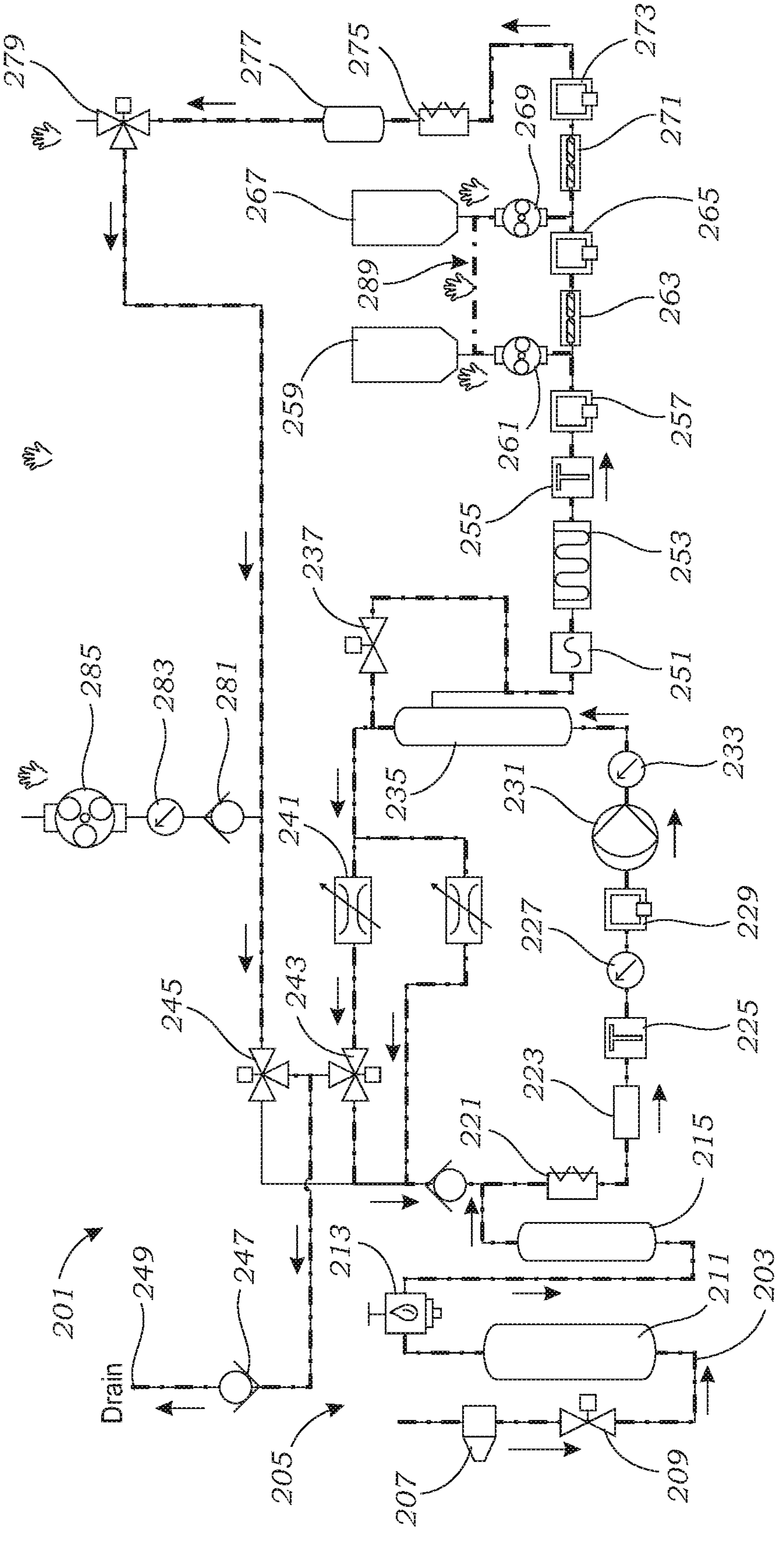
FIG. 9 is the flow chart illustrating the dialysate generator disinfecting one of its drain paths, wherein thicker dashed lines illustrate water capable of moving in the flow path.

In a third disinfecting mode, the dialysate generator 201 disinfects the "drain" pathway leading from valve 245 by recirculating hot water through selected pathways, as illustrated in FIG. 9. This mode requires that the valves, heater, pumps, and ultraviolet disinfectors be activated as follows.

| Actuator FIG. No. | Preferred Actuator Type | Actuator State |
|---|---|---|
| 209 -VPi | 1-Way | Open |
| 237 - VBf | 1-Way | Open |
| 279 - VPo | 3-Way | Recirculate |
| 245 - V5 | 3-Way | To Drain |
| 243 - V8 | 3-Way | Recirculate |
| 253 - HP | Heater | On |
| 231 - ROP | Diaphragm | On |
| 269 - PCP1 | Piston | On |
| 261 - PCP2 | Piston | On |
| 285 - DRP | Gear | Idle |
| 221 - UVi | UV Reactor | Off |
| 275 - UVo | UV Reactor | Off |

Figure 10:
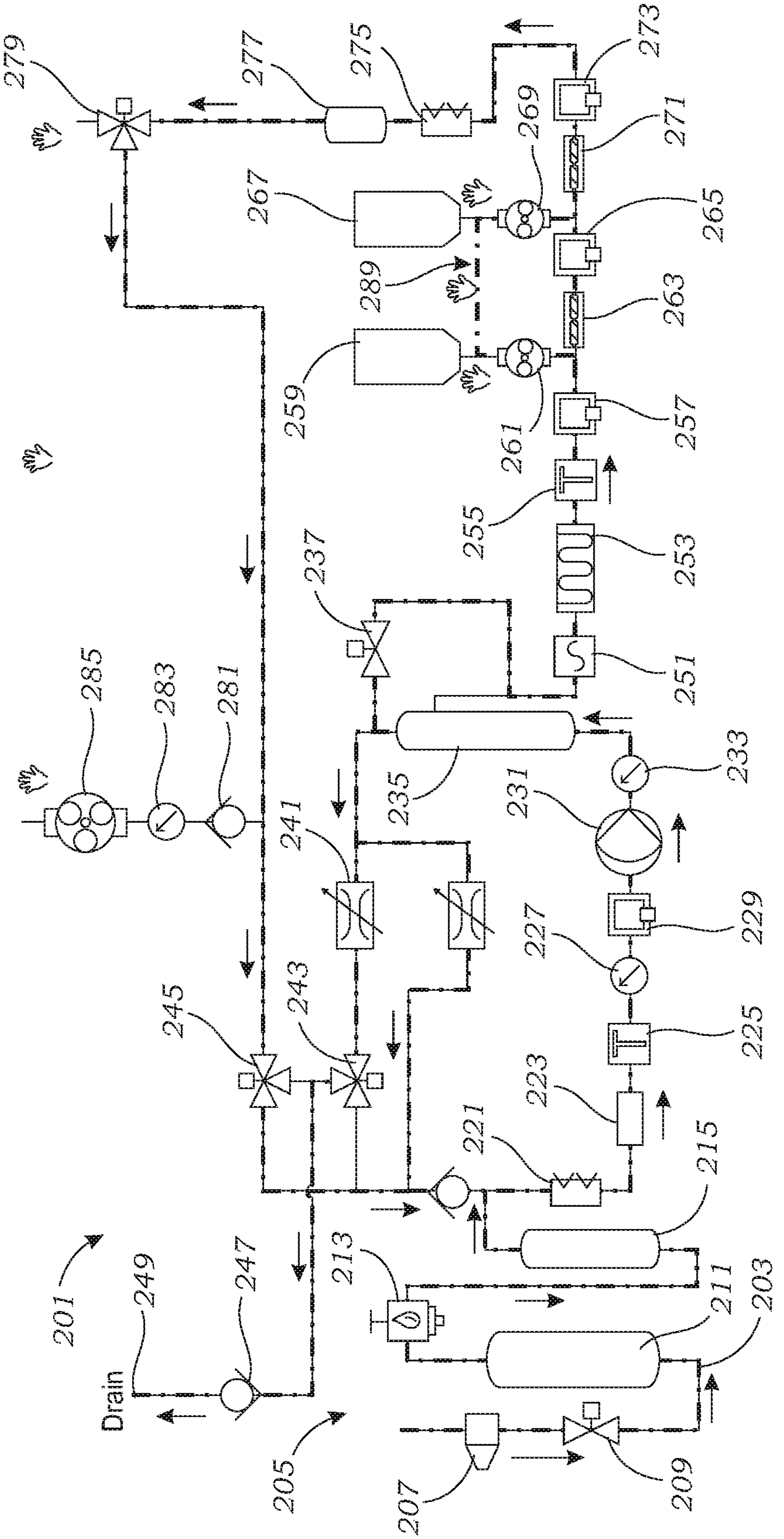
FIG. 10 is the flow chart illustrating the dialysate generator disinfecting one of its drain paths, wherein thicker dashed lines illustrate water capable of moving in the flow path.
Figure 11:
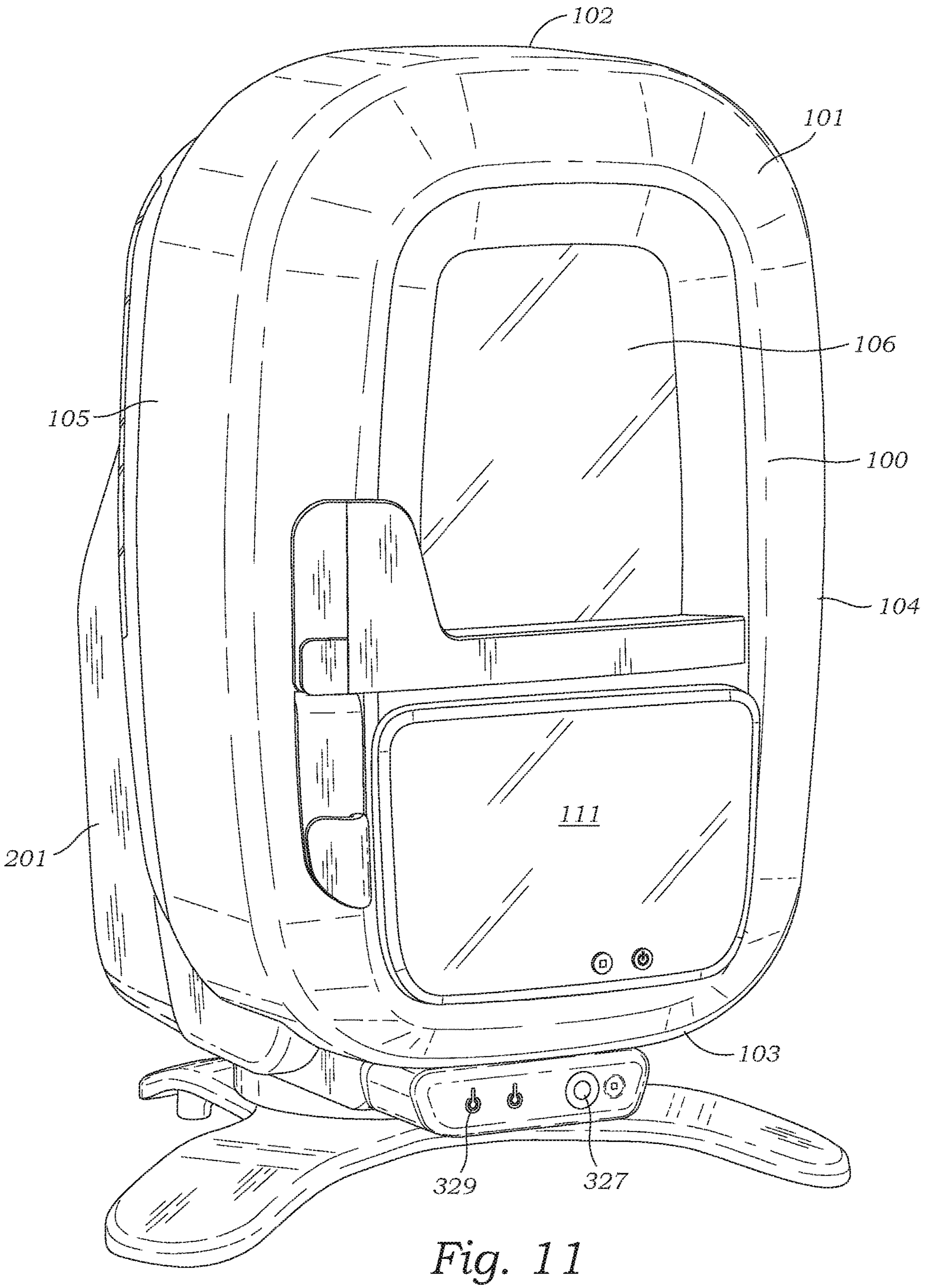
FIG. 11 is a front perspective view of the hemodialysis system.

In a fourth disinfecting mode, the dialysate generator 201 disinfects the "drain" pathway leading from valve 243 by recirculating hot water through selected pathways, as illustrated in FIG. 10. This mode requires that the valves, heater, pumps, and ultraviolet disinfectors be activated as follows.

| Actuator FIG. No. | Preferred Actuator Type | Actuator State |
|---|---|---|
| 209 -VPi | 1-Way | Open |
| 237 - VBf | 1-Way | Open |
| 279 - VPo | 3-Way | Recirculate |
| 245 - V5 | 3-Way | Recirculate |
| 243 - V8 | 3-Way | To Drain |
| 253 - HP | Heater | On |
| 231 - ROP | Diaphragm | On |
| 269 - PCP1 | Piston | On |
| 261 - PCP2 | Piston | On |
| 285 - DRP | Gear | Idle |
| 221 - UVi | UV Reactor | Off |
| 275 - UVo | UV Reactor | Off |

The Hemodialysis Machine and Dialysate Generator Combination

As illustrated in FIGS. 1, 4, 5, and 11-19, the hemodialysis machine 100 and the dialysate generator 201 are standalone machines that may connect or disconnect from one another. To this end, the hemodialysis machine includes a housing 101 for encapsulating and protecting the various components which provide hemodialysis treatment. The hemodialysis machine housing 101 may be constructed in innumerable shapes and sizes so as to physically engage the dialysate generator 201. However, in the preferred embodiment, the hemodialysis machine has a generally hexahedronal shape including substantially a top side 102, a bottom side 103, a left side 104, a right side 105, a front side 106, and a back side 107. In addition, the hemodialysis machine 100 includes one or more electrical connectors 108 for transmitting and receiving electrical signals (and optionally power) between the hemodialysis machine 100 and the dialysate generator. Moreover, as illustrated in FIGS. 1, 4, 5, and 13, the hemodialysis machine 100 includes at least one fluid connector 109 for receiving clean dialysate from the dialysate generator 201, and at least one fluid connector 110 for expelling used dialysate to the dialysate generator. Preferably, the hemodialysis machine includes a touchscreen 111 which is integrated into the machine's housing 101, or is hingedly affixed to the housing 101.

Similarly, the dialysate generator 201 includes a housing 301 for encapsulating and protecting the various components which generate fresh dialysate. The preferred dialysate generator 201 has a housing 301 which has a generally "L" shaped construction including a horizontally extending base unit 303, and a vertically extending back unit 305 which extends vertically from the back of the base unit 303. This construction provides the dialysate generator's housing 301 with a top 307, a bottom 309, a left side 311, a right side 313, a front side 315, and a back side 317. In addition, the horizontally extending base unit 303 provides a resting surface 319 upon which the hemodialysis machine 100 is placed when the hemodialysis machine is mated to the dialysate generator. Preferably, the dialysate generator's processor and pumps are located in its hemodialysis base unit 100, and the dialysate generator's filters and concentrated reagents are located in the dialysis generator back unit 201. These chemical reagents may include the six (6) traditional electrolytes: sodium (Na+), potassium (K+), calcium (Ca2+), magnesium (Mg2+), chloride (Cl—), and bicarbonate as well glucose and/or dextrose. The reservoirs 17 and 20 may be in either the hemodialysis machine as illustrated in FIG. 1, or the reservoirs may be located within the dialysate generator's housing. Moreover, it is preferred that the carbon filter 211, and reverse osmosis membrane 235 be located in elongate cylindrical containers (not shown) that are positioned vertically in the dialysate generator's back unit 305. Also, as illustrated in FIG. 13, preferably the back unit's back side 317 has an openable back panel 318 enabling a person to access all of the disposable components (including the carbon filter 211, secondary filter 215, reverse osmosis membrane 235 and containers of concentrated reagents 259 and 267). The openable back panel 318 may be entirely removed or folded backwardly on hinges so that the disposable components can be easily removed and replaced when depleted.

The dialysate generator 201 includes one or more electrical connectors 325 constructed and positioned upon the dialysate generator's housing 301 for mating to the hemodialysis machine's electrical connector 108. In addition, the dialysate generator 201 includes a first fluid connector 321 which is positioned and passes through the dialysate generator's housing to provide clean dialysate to the hemodialysis machine's fluid connector 109, and the dialysate generator includes a second fluid connector 323 which is positioned and passes through the dialysate generator's housing 301 to receive used dialysate from the hemodialysis machine's fluid connector 110.

In closing, regarding the exemplary embodiments of the present invention as shown and described herein, it will be appreciated that a hemodialysis system is disclosed. The principles of the invention may be practiced in a number of configurations beyond those shown and described, so it is to be understood that the invention is not in any way limited by the exemplary embodiments, but is generally directed to a hemodialysis system and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the Specification is deemed to contain the group as modified.

Unless otherwise indicated, all numbers expressing a characteristic, item, quantity, parameter, property, term, and so forth used in the present Specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the Specification and attached claims are approximations that may vary. At the very least, and not as an attempt to limit the application of the Doctrine of Equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present Specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present Specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

While several particular forms of the invention have been illustrated and described, it will be apparent that various modifications can be made without departing from the spirit and scope of the invention. Therefore, it is not intended that the invention be limited except by the following claims.

The invention claimed is:

1. A hemodialysis system comprising:

a hemodialysis machine including, a dialyzer;

a blood flow path which transports blood through said dialyzer, said blood flow path includes an arterial blood line which connects to a patient's artery and a venous blood line which connects to a patient's vein;

a dialysate flow path, isolated from the blood flow path, which transports dialysate through said dialyzer, said dialysate flow path including a dialysate flow path inlet which receives fresh dialysate and a dialysate flow path outlet which expels used dialysate;

a blood pump which pumps blood through said blood flow path;

a dialysate pump which pumps dialysate through said dialysate flow path;

a primary processor connected to said first and second pumps;

a user interface which is connected to said primary processor;

hemodialysis machine electrical terminals which are electrically connected to said primary processor;

a hemodialysis machine housing wherein said dialysate pump, blood pump, and primary processor are located within said hemodialysis machine housing, and said user interface is affixed to said hemodialysis machine housing;

said hemodialysis system further comprising a dialysate generator machine, said dialysate generator machine comprising, a dialysate generator flow path including a dialysate generator outlet which connects to said dialysate flow path inlet and a dialysate generator inlet which connects to said dialysate flow path outlet;

a source of water connected to said dialysate generator flow path;

a water purification system connected to said dialysate generator flow path which purifies said water;

a source of chemical reagents connected to said dialysate generator flow path which when mixed with said water forms dialysate;

a first reservoir for storing dialysate having a volume between 0.5 liters and 5.0 liters which is in said dialysate flow path to store dialysate and supply dialysate to said dialyzer;

at least one chemical reagent pump which controls the flow of said chemical reagents into said dialysate generator flow path which then mixes with said water to form dialysate;

at least one dialysate generator pump which controls the flow of dialysate through said dialysate generator flow path to said dialysate flow path inlet;

dialysate generator electrical terminals which are electrically connected to said at least one chemical reagent pump and said at least one dialysate generator pump; and a dialysate generator housing wherein said source of water, water purification system, source of chemical reagents, first reservoir, at least one chemical reagent pump, and at least one dialysate generator pump are located within said dialysate generator housing; and said hemodialysis machine is mechanically and electrically connectable and disconnectable to said dialysate generator machine wherein said dialysate flow path inlet is connectable and disconnectable to said dialysate generator outlet, said dialysate flow path outlet is connectable and disconnectable to said dialysate generator inlet, said hemodialysis machine electrical terminals are electrically connectable and disconnectable to said dialysate generator electrical terminals;

said dialysate flow path connecting to said dialysate generator flow path to form a closed loop system wherein said first reservoir supplies dialysate to said dialyzer and said dialyzer supplies spent dialysate back to said first reservoir when said hemodialysis machine is connected to said dialysis generator; and said hemodialysis machine's user interface and primary processor control the operation of both said hemodialysis machine and said dialysate generator including said user interface and primary processor controlling the operation of said blood pump, said dialysate pump, said at least one chemical reagent pump, and said at least one dialysate generator pump.

2. The hemodialysis system of claim 1 further comprising:

said hemodialysis machine electrical terminals are affixed to the exterior of said hemodialysis machine housing and said dialysate generator electrical terminals are affixed to the exterior of said dialysate generator housing, and said hemodialysis machine housing and dialysate generator housing are constructed so that said hemodialysis machine housing can engage and mate to said dialysate generator housing with said dialysate machine electrical terminals mating to said dialysate generator electrical terminals.

3. The hemodialysis system of claim 1 wherein said dialysate generator further comprises a second reservoir for storing dialysate located within said dialysate generator's housing having a volume between 0.5 liters and 5.0 liters, and said second reservoir is in said dialysate flow path to supply dialysate to said dialyzer.

* * * * *